(12) United States Patent
Valmori et al.

(10) Patent No.: US 9,200,047 B2
(45) Date of Patent: Dec. 1, 2015

(54) SSX-2 PEPTIDES PRESENTED BY HLA CLASS II MOLECULES

(75) Inventors: Danila Valmori, Saint Herblain (FR); Maha Ayyoub, Saint Herblain (FR)

(73) Assignee: Ludwig Institute for Cancer Research, Ltd., New York, NY (US)

( * ) Notice: Subject to any disclaimer, the term of this patent is extended or adjusted under 35 U.S.C. 154(b) by 1318 days.

(21) Appl. No.: 13/028,953

(22) Filed: Feb. 16, 2011

(65) Prior Publication Data

US 2011/0144186 A1 Jun. 16, 2011

Related U.S. Application Data

(62) Division of application No. 10/565,315, filed as application No. PCT/US2004/023544 on Jul. 21, 2004, now Pat. No. 7,910,696.

(60) Provisional application No. 60/489,257, filed on Jul. 22, 2003.

(51) Int. Cl.
*A61K 38/00* (2006.01)
*C07K 14/47* (2006.01)

(52) U.S. Cl.
CPC ............ *C07K 14/4748* (2013.01); *A61K 38/00* (2013.01)

(58) Field of Classification Search
CPC . C07K 14/4748; C07K 2319/01; A61K 38/00
USPC .......................................... 514/448; 536/23.5
See application file for complete search history.

(56) References Cited

U.S. PATENT DOCUMENTS

| | | | |
|---|---|---|---|
| 5,840,839 A | 11/1998 | Wang et al. | |
| 6,140,050 A | 10/2000 | Sahin et al. | |
| 6,287,756 B1 | 9/2001 | Tureci et al. | |
| 6,338,947 B1 | 1/2002 | Sahin et al. | |
| 6,548,064 B1 | 4/2003 | Tureci et al. | |

FOREIGN PATENT DOCUMENTS

| | | |
|---|---|---|
| WO | WO 96/02641 A2 | 2/1996 |
| WO | WO 00/00642 A | 1/2000 |
| WO | WO 00/20581 A1 | 4/2000 |
| WO | WO 01/23560 A | 4/2001 |
| WO | WO 01/82963 A | 11/2001 |
| WO | WO 03/008537 A2 | 1/2003 |

OTHER PUBLICATIONS

WO 9602641 (Cooper et al. Feb. 1996) sequence search alignments for SEQ ID Nos. 1-8.
WO 2003008537 (Simard et al. Jan. 2003) sequence search alignments for SEQ ID Nos. 1-8.
Arnold et al., Reliable generation and use of MHC class II:gamma2aFc multimers for the identification of antigen-specific CD4(+) T cells. J Immunol Methods. Dec. 20, 2002;271(1-2):137-51.
Ayyoub et al., Identification of an SSX-2 epitope presented by dendritic cells to circulating autologous CD4+ T cells. J Immunol. Jun. 1, 2004;172(11):7206-11.
Ayyoub et al., Proteasome-assisted identification of a SSX-2-derived epitope recognized by tumor-reactive CTL infiltrating metastatic melanoma. J Immunol. Feb. 15, 2002;168(4):1717-22.
Bowie et al., Deciphering the message in protein sequences: tolerance to amino acid substitutions. Science. Mar. 16, 1990;247(4948):1306-10.
Coulie, Antigens recognized on human tumors by cytolytic T lymphocytes: towards vaccination? Stem Cells. Jul. 1995;13(4):393-403.
Rubio-Godoy et al., Combinatorial peptide library-based identification of peptide ligands for tumor-reactive cytolytic T lymphocytes of unknown specificity. Eur J Immunol. Aug. 2002;32(8):2292-9.
Sanderson et al., Expression of endogenous peptide-major histocompatibility complex class II complexes derived from invariant chain-antigen fusion proteins. Proc Natl Acad Sci U S A. Aug. 1, 1995;92(16):7217-21.
Schirle et al., Combining computer algorithms with experimental approaches permits the rapid and accurate identification of T cell epitopes from defined antigens. J Immunol Methods. Nov. 1, 2001;257(1-2):1-16.
Wagner et al., Identification of HLA-A*0201 binding antigenic peptides derived from the HOM-MEL-40/SSX-2 antigen that stimulate CTL from patients with SSX-2 positive cancers, Proceedings of the American Association for Cancer Research Annual Meeting; Mar. 2002; vol. 43, p. 606.

*Primary Examiner* — Lynn Bristol
(74) *Attorney, Agent, or Firm* — Wolf, Greenfield & Sacks, P.C.

(57) ABSTRACT

The invention describes HLA class II binding peptides encoded by the SSX-2 tumor associated gene, as well as nucleic acids encoding such peptides and antibodies relating thereto. The peptides stimulate the activity and proliferation of CD4+ T lymphocytes. Methods and products also are provided for diagnosing and treating conditions characterized by expression of the SSX-2 gene.

8 Claims, 6 Drawing Sheets

| Peptides | %CD4+ IFN-γ+ | %CD4+ IL-2+ |
|---|---|---|
| None | 0.09 | 0.02 |
| SSX-2 P1-3: 1-22, 13-34, 25-46 | 1.17 | 0.39 |
| SSX-2 P4-6: 37-58, 49-70, 61-82 | 0.29 | 0.05 |
| SSX-2 P7-9: 73-94, 87-105, 97-118 | 0.13 | 0.04 |
| SSX-2 P10-12: 109-130, 121-142, 133-154 | 0.09 | 0.01 |
| SSX-2 P13-15: 145-166, 157-178, 169-188 | 0.17 | 0.03 |

SSX-2 PEPTIDES PRESENTED BY HLA CLASS II MOLECULES

RELATED APPLICATIONS

This application is a divisional of U.S. patent application Ser. No. 10/565,315, filed Apr. 19, 2006, now issued as U.S. Pat. No. 7,910,696, which is a national stage filing under 35. U.S.C. §371 of PCT international patent application PCT/US04/23544, filed Jul. 21, 2004, which was published under PCT Article 21(2) in English, and which claims priority under 35 U.S.C. §119 to U.S. provisional patent application Ser. No. 60/489,257, filed Jul. 22, 2003, the entire contents of each of which are incorporated herein by reference.

FIELD OF THE INVENTION

This invention relates to fragments of the tumor associated gene product SSX-2 which bind to and are presented to T lymphocytes by HLA class II molecules. The peptides, nucleic acid molecules which code for such peptides, as well as related antibodies and CD4+ T lymphocytes, are useful, inter alia, in diagnostic and therapeutic contexts.

BACKGROUND OF THE INVENTION

The process by which the mammalian immune system recognizes and reacts to foreign or alien materials is complex. An important facet of the system is the T cell response, which in part comprises mature T lymphocytes which are positive for either CD4 or CD8 cell surface proteins. T lymphocytes can recognize and interact with other cells via cell surface complexes of peptides and molecules referred to as human leukocyte antigens ("HLAs") or major histocompatibility complexes ("MHCs"). These peptides are derived from larger molecules which are processed by the cells which also present the HLA/MHC molecule. See Male et al., *Advanced Immunology* (J.P. Lipincott Company, 1987), especially chapters 6-10. The interaction of T cells and complexes of HLA/peptide is restricted, requiring a specific T cell for a specific complex of an HLA molecule and a peptide. If a specific T cell is not present, there is no T cell response even if its partner complex is present. Similarly, there is no response if the specific complex is absent, but the T cell is present. The mechanisms described above are involved in the immune system's response to foreign materials, in autoimmune pathologies, cellular abnormalities, and in responses to cancer.

The ability of the T cell arm of the tumor immune response to distinguish tumor cells from normal tissues with exquisite specificity, provides the basis for the development of T cell based cancer immunotherapy. This specific recognition is the result of the preferential or exclusive expression of some antigens in tumors as compared to normal tissues. Several categories of antigens with more or less tumor-restricted expression have been identified during the last decade. Most of them correspond to non mutated self-antigens with tissue restricted expression, although tumor-specific mutated antigens have also been identified (Robbins et al., *J Exp Med*, 1996, 183:1185-1192). Tissue-specific differentiation antigens such as Melan-A or gp100 (Kawakami et al, *J Exp Med*, 1994, 180:347-352; Coulie, *J Exp Med*, 1994. 180:35-42) expressed by both normal cells of the melanocytic lineage and malignant melanoma cells, and often spontaneously immunogenic in melanoma patients, have been extensively studied. The group of tumor antigens most relevant for the development of generic cancer vaccines, however, is that of the so-called cancer/testis antigens (CTA) (Scanlan et al. *Immunol Rev* 2002. 188:22-32), whose gene expression is developmentally regulated, being mostly restricted to gametogenic cells but silent in adult normal cells. Possibly as the result of activation of a common gametogenic protein expression program in cancer cells (Old et al. *Cancer Immunity* 2001. 1:1). CTA are expressed in variable proportions of tumors of different histological types.

Numerous MHC Class I restricted epitopes recognized by tumor reactive CD8+ T cells and specific for antigens in each of the groups listed above have been identified. Interestingly, spontaneous CD8+ T cell responses directed against several of these epitopes have been detected in cancer patients (Valmori et al, *Cancer Res,* 2000. 60:4499-4506; Valmori et al., *Cancer Res,* 2001, 61:501-512). In contrast, the identification of MHC Class II restricted epitopes recognized by tumor antigen specific CD4+ T cells has proven to be more difficult possibly because of the relatively low frequency of the latter and/or to the lack of effective identification methods (Klenerman et al, *Nat Rev Immunol,* 2002, 2:263-272). Lately, however, because of important technical advances, the identification of CD4+ T cell epitopes derived from tumor antigens including CTA has been reported with increasing frequency (Chaux et al. *J Exp Med* 1999. 189:767-778; Zeng et al. *Proc Natl Acad Sci USA* 2001. 98:3964-3969).

Because most nonhematopoietic tumors express MHC Class I but not Class II molecules, it has been assumed that the predominant antitumor T cell mediated effector mechanism in vivo is direct killing of tumor cells by tumor antigen specific CD8+ T lymphocytes (CTL). CTL can indeed directly and efficiently lyse tumor cells resulting sometimes in in vivo regression of large tumor masses. It is, however, becoming increasingly clear that both tumor antigen specific CD8+ and CD4+ T cell responses are important for efficient tumor immune response to occur in vivo (Wang, *Trends Immunol.* 2001. 22:269-276).

The multiple roles that tumor antigen specific CD4+ T cells can potentially play in mediating antitumor functions are being progressively unveiled. These involve different to mechanisms from providing help for both priming and maintenance of tumor antigen specific CD8+ T cells, to activation of B cells for production of tumor antigen specific antibodies, and even including more direct effects in the effector phase of tumor rejection. The identification of CD4+ T cell epitopes toward which spontaneous responses arise in cancer patients is of particular interest as it gives the opportunity to analyze such responses and their underlying molecular mechanisms in vivo. Furthermore, there exist many patients who would not benefit from any therapy which includes helper T cell stimulation via the aforementioned peptides. Accordingly, there is a need for the identification of additional tumor associated antigens which contain epitopes presented by MHC Class II molecules and recognized by CD4+ lymphocytes.

SUMMARY OF THE INVENTION

It now has been discovered that the SSX-2 gene (also known as HOM-MEL-40) encodes HLA class II binding peptides that are epitopes presented by HLA-DP. These peptides, when presented by an antigen presenting cell having the appropriate HLA class II molecule, effectively induce the activation and proliferation of CD4+ T lymphocytes.

The invention provides isolated SSX-2 peptides which bind HLA class II molecules, and functional variants of such peptides. The functional variants contain one or more amino acid additions, substitutions or deletions to the SSX-2 peptide sequence. The invention also provides isolated nucleic acid molecules encoding such peptides, expression vectors containing those nucleic acid molecules, host cells transfected with those nucleic acid molecules, and antibodies to those peptides and complexes of the peptides and HLA class II antigen presenting molecules. T lymphocytes which recognize complexes of the peptides and HLA class II antigen presenting molecules are also provided. Kits and vaccine compositions containing the foregoing molecules additionally are provided. The foregoing can be used in the diagnosis or treatment of conditions characterized by the expression of SSX-2. As it is known that the members of the SSX family of polypeptides and nucleic acids share significant sequence identity and functional homology (e.g., as tumor antigens and precursors), the invention also embraces HLA binding peptides of similar amino acid sequence derived from members of the SSX family other than SSX-2 (see, e.g., Table III). Therefore, it is understood that the disclosure contained herein of SSX-2 HLA class II to binding peptides, compositions containing such peptides, and methods of identifying and using such peptides applies also to other members of the SSX tumor associated antigen family.

According to one aspect of the invention, isolated SSX-2 HLA class II-binding peptides are provided. The peptides include an amino acid sequence set forth as SEQ ID NO:8, or a functional variant thereof comprising 1-5 amino acid substitutions. The HLA class II-binding peptide or functional variant does not include a full length SSX protein, particularly a full length SSX-2 protein. In certain embodiments, the isolated includes comprises an amino acid sequence selected from the group consisting of SEQ ID NO:1, SEQ ID NO:2, SEQ ID NO:3, SEQ ID NO:4, SEQ ID NO:5, SEQ ID NO:6 and SEQ ID NO:7. Preferably the isolated peptide consists of an amino acid sequence selected from the group consisting of SEQ ID NO:1, SEQ ID NO:5, and SEQ ID NO:6, most preferably SEQ ID NO:1. Preferred functional variants include SEQ ID NOs:40-42 and SEQ ID NOs:44-48, as shown in Table III, and fragments thereof that bind HLA class II molecules.

In further embodiments, the isolated peptide includes an endosomal targeting signal, preferably including an endosomal targeting portion of human invariant chain Ii.

In other embodiments, the isolated peptide is non-hydrolyzable. Preferred non-hydrolyzable peptides include peptides comprising D-amino acids, peptides comprising a -psi[CH₂NH]-reduced amide peptide bond, peptides comprising a -psi[COCH₂]-ketomethylene peptide bond, peptides comprising a -psi[CH(CN)NH]-(cyanomethylene)amino peptide bond, peptides comprising a -psi[CH₂CH(OH)]-hydroxyethylene peptide bond, peptides comprising a -psi[CH₂O]-peptide bond, and peptides comprising a -psi[CH₂S]-thiomethylene peptide bond.

According to another aspect of the invention, compositions are provided that include an isolated HLA class I-binding peptide and an isolated SSX-2 HLA class II-binding peptide. The isolated SSX-2 HLA class II-binding peptide includes an amino acid sequence set forth as SEQ ID NO:8, or a functional variant thereof comprising 1-5 amino acid substitutions (but not including the full length of a SSX protein, particularly a full length SSX-2 protein). Preferably the HLA class I-binding peptide and the SSX-2 HLA class II-binding peptide are combined as a polytope polypeptide.

In preferred embodiments, the isolated SSX-2 HLA class II-binding peptide includes to an amino acid sequence selected from the group consisting of SEQ ID NO:1, SEQ ID NO:2, SEQ ID NO:3, SEQ ID NO:4, SEQ ID NO:5, SEQ ID NO:6 and SEQ ID NO:7; most preferably the isolated SSX-2 HLA class II-binding peptide consists of the amino acid sequence set forth as SEQ ID NO:1. Preferred functional variants include SEQ ID NOs:40-42 and SEQ ID NOs:44-48, as shown in Table III, and fragments thereof that bind HLA class II molecules.

In further embodiments, the isolated SSX-2 HLA class II-binding peptide includes an endosomal targeting signal, preferably including an endosomal targeting portion of human invariant chain Ii.

According to a further aspect of the invention, compositions including one or more of the foregoing isolated SSX-2 HLA class II-binding peptides complexed with one or more isolated HLA class II molecules are provided. Preferably the number of isolated SSX-2 HLA class II-binding peptides and the number of isolated HLA class II molecules are equal. More preferably, the isolated SSX-2 HLA class II-binding peptides and the isolated HLA class II molecules are coupled as a tetrameric molecule of individual isolated SSX-2 HLA class II-binding peptides bound to individual isolated HLA class II molecules. Even more preferably, the HLA class II molecules are DP molecules.

According to still another aspect of the invention, isolated nucleic acid molecules are provided that encode the foregoing SSX-2 HLA class II-binding peptides, provided that the nucleic acid molecule does not encode a full length SSX protein, particularly a full length SSX-2 protein. Also provided are expression vectors including these isolated nucleic acid molecules operably linked to a promoter. In certain embodiments, the nucleic acid molecule includes a nucleotide sequence selected from the group consisting of SEQ ID NO:15, SEQ ID NO:16, SEQ ID NO:17, SEQ ID NO:18 SEQ ID NO:19 SEQ ID NO:20 and SEQ ID NO:21, preferably SEQ ID NO:15. The foregoing expression vectors, in other embodiments, also include a nucleic acid molecule that encodes an HLA-DP molecule. Host cells transfected or transformed with the foregoing expression vectors also are provided; in some embodiments, the host cell expresses an HLA-DP molecule.

In another aspect of the invention, methods for selectively enriching a population of T lymphocytes with CD4⁺ T lymphocytes specific for a SSX-2 HLA class II-binding peptide are provided. The methods include contacting an isolated population of T lymphocytes with an to agent presenting a complex of the SSX-2 HLA class II-binding peptide and an HLA class II molecule in an amount sufficient to selectively enrich the isolated population of T lymphocytes with the CD4⁺ T lymphocytes.

According to another aspect of the invention, methods for diagnosing a cancer characterized by expression of SSX-2 HLA class II-binding peptide are provided. The methods include contacting a biological sample isolated from a subject with an agent that is specific for the SSX-2 HLA class II-binding peptide, and determining the interaction between the agent and the SSX-2 HLA class II-binding peptide as a determination of the disorder. Preferably the agent is an antibody or an antigen binding fragment thereof.

According to yet another aspect of the invention, methods for diagnosing a cancer characterized by expression of a SSX-2 HLA class II-binding peptide which forms a complex with an HLA class II molecule are provided. The methods include contacting a biological sample isolated from a subject with an agent that binds the complex, and determining binding between the complex and the agent as a determination of the disorder.

In still a further aspect of the invention, methods for treating a subject having a cancer characterized by expression of SSX-2 HLA class II-binding peptide are provided. The methods include administering to the subject an amount of a SSX-2 HLA class II-binding peptide effective to ameliorate the disorder.

According to a further aspect of the invention, additional methods for treating a subject having a cancer characterized by expression of SSX-2 HLA class II-binding peptide are provided. These methods include administering to the subject an amount of a HLA class I-binding peptide and an amount of a SSX-2 HLA class II-binding peptide effective to ameliorate the disorder. In some preferred embodiments, the HLA class I-binding peptide and the SSX-2 HLA class II-binding peptide are combined as a polytope polypeptide. Preferably the HLA class I-binding peptide is a SSX-2 HLA class I-binding peptide.

According to another aspect of the invention, methods for treating a subject having a cancer characterized by expression of SSX-2 are provided. The methods include administering to the subject an amount of a SSX-2 HLA class II-binding peptide effective to ameliorate the cancer.

In another aspect of the invention, methods are provided for treating a subject having a cancer characterized by expression of SSX-2 HLA class II-binding peptide. The methods to include administering to the subject an amount of autologous CD4+ T lymphocytes sufficient to ameliorate the disorder, wherein the CD4+ T lymphocytes are specific for complexes of an HLA class II molecule and a SSX-2 HLA class II-binding peptide.

In the foregoing methods, the SSX-2 HLA class II-binding peptide preferably includes an amino acid sequence set forth as SEQ ID NO:8, or a functional variant thereof comprising 1-5 amino acid substitutions. In certain preferred embodiments of the foregoing methods, the SSX-2 HLA class II-binding peptide includes an amino acid sequence selected from the group consisting of SEQ ID NO:1, SEQ ID NO:2, SEQ ID NO:3, SEQ ID NO:4, SEQ ID NO:5, SEQ ID NO:6 and SEQ ID NO:7. More preferably, the SSX-2 HLA class II-binding peptide consists of an amino acid sequence selected from the group consisting of SEQ ID NO:1, SEQ ID NO:5 and SEQ ID NO:6, most preferably SEQ ID NO:1. Preferred functional variants include SEQ ID NOs:40-42 and SEQ ID NOs:44-48, as shown in Table III, and fragments thereof that bind HLA class II molecules. In some embodiments, the HLA class II molecule is an HLA-DP molecule. In other embodiments, the SSX-2 HLA class II binding peptide includes an endosomal targeting signal, preferably an endosomal targeting portion of human invariant chain Ii.

In a further aspect of the invention, methods for identifying functional variants of a SSX-2 HLA class II-binding peptide are provided. The methods include selecting a SSX-2 HLA class II-binding peptide which includes an amino acid sequence selected from the group consisting of SEQ ID NO:1, SEQ ID NO:2, SEQ ID NO:3, SEQ ID NO:4, SEQ ID NO:5, SEQ ID NO:6 and SEQ ID NO:7, an HLA class II-binding molecule which binds the SSX-2 HLA class II-binding peptide, and a T cell which is stimulated by the SSX-2 HLA class II-binding peptide presented by the HLA class II-binding molecule; mutating a first amino acid residue of the SSX-2 HLA class II-binding peptide to prepare a variant peptide; and determining the binding of the variant peptide to HLA class II-binding molecule and the stimulation of the T cell. Binding of the variant peptide to the HLA class II-binding molecule and stimulation of the T cell by the variant peptide presented by the HLA class II-binding molecule indicates that the variant peptide is a functional variant. Exemplary functional variants that can be tested using such methods and used as controls in such methods include the preferred functional variants (SEQ ID NOs:40-42 and SEQ ID NOs:44-48, and fragments thereof that bind HLA class II molecules).

In some embodiments, the methods include a step of comparing the stimulation of the T cell by the SSX-2 HLA class II-binding peptide and the stimulation of the T cell by the functional variant as a determination of the effectiveness of the stimulation of the T cell by the functional variant.

According to another aspect of the invention, isolated polypeptides are provided that bind selectively the foregoing SSX-2 HLA class II-binding peptides, provided that the isolated polypeptide is not an HLA class II molecule. Also provided are isolated polypeptides that bind selectively a complex of the foregoing SSX-2 HLA class II-binding peptides and an HLA class II molecule, provided that the isolated polypeptide is not a T cell receptor. The foregoing isolated polypeptides preferably are antibodies, more preferably monoclonal antibodies. Preferred monoclonal antibodies include human antibodies, humanized antibodies, chimeric antibodeis and single chain antibodies. In other embodiments, the isolated polypeptides are antibody fragments selected from the group consisting of Fab fragments, $F(ab)_2$ fragments, Fv fragments or fragments including a CDR3 region selective for a SSX-2 HLA class II-binding peptide.

The invention also provides isolated CD4+ T lymphocytes that selectively bind a complex of an HLA class II molecule and a SSX-2 HLA class II-binding peptide, preferably wherein the HLA class II molecule is an HLA-DP molecule and wherein the SSX-2 HLA class II-binding peptide includes an amino acid sequence set forth as SEQ ID NO:8 or a functional variant thereof. More preferably, the SSX-2 HLA class II-binding peptide includes an amino acid sequence selected from the group consisting of SEQ ID NO:1, SEQ ID NO:2, SEQ ID NO:3, SEQ ID NO:4, SEQ ID NO:5, SEQ ID NO:6 and SEQ ID NO:7. Still more preferably, the SSX-2 HLA class II-binding peptide consists of an amino acid sequence selected from the group consisting of SEQ ID NO:1, SEQ ID NO:5, and SEQ ID NO:6, most preferably SEQ ID NO:1. Preferred functional variants include SEQ ID NOs:40-42 and SEQ ID NOs:44-48, as shown in Table III, and fragments thereof that bind HLA class II molecules.

In a further aspect, the invention provides isolated antigen presenting cells that include a complex of an HLA class II molecule and a SSX-2 HLA class II-binding peptide, preferably wherein the HLA class II molecule is an HLA-DP molecule and wherein the SSX-2 HLA class II-binding peptide comprises an amino acid sequence set forth as SEQ ID NO:8 or a functional variant thereof. More preferably, the SSX-2 HLA class II-binding peptide includes to an amino acid sequence selected from the group consisting of SEQ ID NO:1, SEQ ID NO:2, SEQ ID NO:3, SEQ ID NO:4, SEQ ID NO:5, SEQ ID NO:6 and SEQ ID NO:7. Still more preferably, the SSX-2 HLA class II-binding peptide consists of an amino acid sequence selected from the group consisting of SEQ ID NO:1, SEQ ID NO:5, and SEQ ID NO:6, most preferably SEQ ID NO:1. Preferred functional variants include SEQ ID NOs:40-42 and SEQ ID NOs:44-48, as shown in Table III, and fragments thereof that bind HLA class II molecules.

According to another aspect of the invention, methods for identification of HLA class II-binding epitopes of a protein are provided. The methods include obtaining a peptide library of peptides that span the amino acid sequence of the protein; and contacting a population of cells containing CD4+ T lymphocytes with the peptide library in the presence of antigen presenting cells to stimulate proliferation and/or cytokine production by CD4+ T lymphocytes that selectively bind a peptide in the peptide library. The stimulation of CD4+ T lymphocytes indicates that a peptide in the library contains at least one HLA class II epitope. In certain embodiments, the peptides are at least about 12 amino acids in length. In other embodiments, the peptides are between about 14 and about 50 amino acids in length. Preferably the peptides are between about 20 and about 22 amino acids in length.

In other embodiments, the peptides overlap each other by at least about 4 amino acids, more preferably by at least about 10 amino acids.

In still other embodiments, the antigen presenting cells are autologous peripheral blood mononuclear cells.

The method can include additional steps of screening the isolated CD4+ T lymphocytes with submixtures or single peptides, and/or clonally expanding the stimulated CD4+ T lymphocytes by periodic stimulation with the selected peptide and/or isolating the stimulated CD4+ T lymphocytes. In the last case, it is preferred that the isolation of the stimulated CD4+ T lymphocytes is carried out by cytokine guided flow cytometry cell sorting.

In some embodiments, the population of cells containing CD4+ T lymphocytes also includes CD8+ T lymphocytes. In these embodiments, the stimulation of both CD4+ and CD8+ T lymphocytes indicates that a peptide in the synthetic library contains both HLA class I and HLA class II epitopes.

The invention also provides pharmaceutical preparations containing any one or more of the medicaments described above or throughout the specification. Such pharmaceutical preparations can include pharmaceutically acceptable diluents, carriers and/or excipients.

The use of the foregoing compositions, peptides, cells and nucleic acids in the preparation of a medicament, particularly a medicament for treatment of cancer, or for treating an immune response is also provided.

These and other objects of the invention will be described in further detail in connection with the detailed description of the invention.

BRIEF DESCRIPTION OF THE DRAWINGS

FIG. 3A: Intracellular IFN-γ secretion by SSX-2 specific CD4+ T cells (clone 3C8) upon stimulation with peptide SSX-2$_{13-34}$ was assessed both in the absence and in the presence of anti HLA-DR, -DP or -DQ antibodies. FIG. 3B: The ability of APC bearing different HLA-DP alleles to present peptide SSX-2 13-34 to specific CD4+ T cells was assessed by intracellular IFN-γ secretion.

FIG. 4A: Recognition of Me 260 cells by CD4+ T cells was tested by ELISPOT in the absence or in the presence of exogeneously added peptide SSX-2$_{13-34}$. Where indicated, cells were treated with IFN-γ during 48 hr. FIG. 4B: Recognition of T465A was assessed as in FIG. 3A as well as upon transfection with an SSX-2 encoding plasmid. The CD8+ T cell clone B3.4 specific for peptide SSX-2 41-49 was used as an internal control.

FIG. 5A: The ability of EBV LAU 149 to process the SSX-2 protein and present the relevant epitope to specific CD4+ T cells was assessed by ELISPOT after 12 hrs incubation with soluble recombinant SSX-2 protein followed by washing. NY-ESO-1 protein was used as an internal control. FIGS. 5B and 5C: Processing and presentation of the SSX-2 CD4+ T cell epitope by LAU 672 autologous monocyte-derived DC was assessed as in FIG. 5A.

BRIEF DESCRIPTION OF THE SEQUENCES

Figures 1A, 1B:
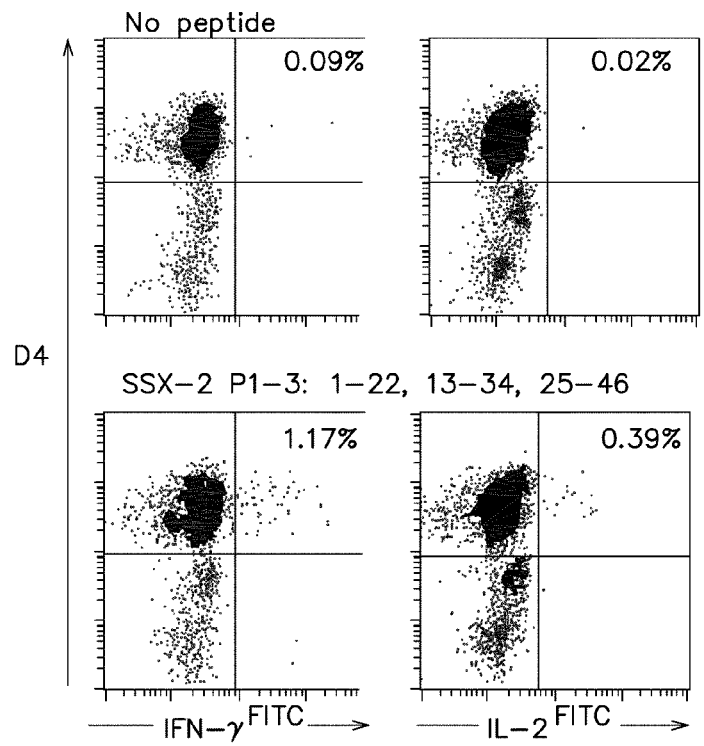
FIGS. 1A and 1B show detection of SSX-2 specific CD4+ T cells in peptide stimulated cultures. The presence of specific CD4+ T cells in the culture from patient LAU 672 was assessed by intracellular staining with anti-IFN-γ (FIG. 1A, left panels) or anti-IL-2 antibodies (FIG. 1A, right panels) after stimulation with autologous PBMC alone (upper panels) or with the peptide submixture P1-3 (containing SSX-2 peptides 1-22, 13-34, 25-46). Numbers in upper right quadrants are percent of cytokine producing cells among CD4+ T cells. The data obtained for all peptide submixtures is shown in FIG. 1B.

SEQ ID NO:1 is a SSX-2$_{13-34}$ peptide (VGAQIPE-KIQKAFDDIAKYFSK).

SEQ ID NO:2 is a SSX-2$_{13-36}$ peptide (VGAQIPE-KIQKAFDDIAKYFSKEE).

SEQ ID NO:3 is a SSX-2$_{13-32}$ peptide (VGAQIPE-KIQKAFDDIAKYF).

SEQ ID NO:4 is a SSX-2$_{13-30}$ peptide (VGAQIPE-KIQKAFDDIAK).

SEQ ID NO:5 is a SSX-2$_{17-34}$ peptide (IPEKIQKAFDDI-AKYFSK).

SEQ ID NO:6 is a SSX-2$_{19-34}$ peptide (EKIQKAFDDI-AKYFSK).

SEQ ID NO:7 is a SSX-2$_{21-34}$ peptide (IQKAFDDI-AKYFSK).

SEQ ID NO:8 is a SSX-2$_{19-30}$ peptide (EKIQKAFD-DIAK).

SEQ ID NOs:9 and 10 are the nucleotide and amino acid sequences, respectively, for SSX-2 peptide isoform b/transcript variant 2 (nucleic acid=NM_175698.1, GI:28559005; polypeptide=NP_783629.1 GI:28559006).

SEQ ID NOs:11 and 12 are the nucleotide and amino acid sequences, respectively, for SSX-2 peptide isoform a/transcript variant 1 (nucleic acid=NM_003147.4, GI:28559004; polypeptide=NP_003138.3 GI:27659724).

SEQ ID NOs:13 and 14 are nucleotide and amino acid sequences, respectively, for a protein that is similar to SSX-2 isoform b/transcript variant 2 (nucleic acid=XM_300501.1, GI:30157775; polypeptide=XP_300501.1, GI:30157776).

SEQ ID NO:15 is a nucleotide sequence encoding the SSX-2 peptide SSX-2$_{13-34}$ (SEQ ID NO:1): gtt ggg gcc caa att ccc gaa aaa atc caa aaa gcn ttt gat gat att gcn aaa tat ttt agt aaa.

SEQ ID NO:16 is a nucleotide sequence encoding the SSX-2 peptide SSX-2$_{13-36}$ (SEQ ID NO:2): gtt ggg gcc caa att ccc gaa aaa atc caa aaa gcn ttt gat gat att gcn aaa tat ttt agt aaa gaa gaa).

SEQ ID NO:17 is a nucleotide sequence encoding the SSX-2 peptide SSX-2$_{13-32}$ (SEQ ID NO:3): gtt ggg gcc caa att ccc gaa aaa atc caa aaa gcn ttt gat gat att gcn aaa tat ttt.

SEQ ID NO:18 is a nucleotide sequence encoding the SSX-2 peptide SSX-2$_{13-30}$ (SEQ ID NO:4): gtt ggg gcc caa att ccc gaa aaa atc caa aaa gcn ttt gat gat att gcn aaa.

SEQ ID NO:19 is a nucleotide sequence encoding the SSX-2 peptide SSX-2$_{17-34}$ (SEQ ID NO:5): att ccc gaa aaa atc caa aaa gcn ttt gat gat att gcn aaa tat ttt agt aaa.

SEQ ID NO:20 is a nucleotide sequence encoding the SSX-2 peptide SSX-2$_{19-34}$ (SEQ ID NO:6): gaa aaa atc caa aaa gcn ttt gat gat att gcn aaa tat ttt agt aaa.

SEQ ID NO:21 is a nucleotide sequence encoding the SSX-2 peptide SSX-2$_{21-34}$ (SEQ ID NO:7): gaa aaa atc caa aaa gcn ttt gat gat att gcn aaa tat ttt agt aaa.

SEQ ID NO:22 is the nucleotide sequence of the DPA forward primer (atg cgc cct gaa gac aga atg t).

SEQ ID NO:23 is the nucleotide sequence of the DPA reverse primer (tca cag ggt ccc ctg ggc ccg ggg ga).

SEQ ID NO:24 is the nucleotide sequence of the DPB forward primer (atg atg gtt ctg cag gtt tct g).

SEQ ID NO:25 is the nucleotide sequence of the DPB reverse primer (tta tgc aga tcc tcg ttg aac ttt c).

SEQ ID NO:26 is a SSX-2$_{1-22}$ peptide (MNGDDAFARRPTVGAQIPEKIQ).

SEQ ID NO:27 is a SSX-2$_{25-46}$ peptide (FDDIAKYFSKEEWEKMKASEKI).

SEQ ID NO:28 is a SSX-2$_{37-58}$ peptide (WEKMKASEKIFYVYMKRKYEAM).

SEQ ID NO:29 is a SSX-2$_{49-70}$ peptide (VYMKRKYEAMTKLGFKATLPPF).

SEQ ID NO:30 is a SSX-2$_{61-82}$ peptide (LGFKATLPPFMCNKRAEDFQGN).

SEQ ID NO:31 is a SSX-2$_{73-94}$ peptide (NKRAEDFQGNDLDNDPNRGNQV).

SEQ ID NO:32 is a SSX-2$_{87-105}$ peptide (DPNRGNQVERPQMTFGRLQ).

SEQ ID NO:33 is a SSX-2$_{97-118}$ peptide (PQMTFGRLQGISPKIMPKKPAE).

SEQ ID NO:34 is a SSX-2$_{109-130}$ peptide (PKIMPKKPAEEGNDSEEVPEAS).

SEQ ID NO:35 is a SSX-2$_{121-142}$ peptide (NDSEEVPEASGPQNDGKELCPP).

SEQ ID NO:36 is a SSX-2$_{133-154}$ peptide (QNDGKELCPPGKPTTSEKIHER).

SEQ ID NO:37 is a SSX-2$_{145-166}$ peptide (PTTSEKIHERSGPKRGEHAWTH).

SEQ ID NO:38 is a SSX-2$_{157-178}$ peptide (PKRGEHAWTHRLRERKQLVIYE).

SEQ ID NO:39 is a SSX-2$_{169-188}$ peptide (RERKQLVIYEEISDPEEDDE).

SEQ ID NO:40 is a SSX-1$_{13-34}$ peptide (DDAKASEKRSKAFDDIATYFSK).

SEQ ID NO:41 is a SSX-3$_{13-34}$ peptide (VGAQIPEKIQKAFDDIAKYFSK).

SEQ ID NO:42 is a SSX-4$_{13-34}$ peptide (DDAQISEKLRKAFDDIAKYFSK).

SEQ ID NO:43 is a SSX-5$_{13-34}$ (isoform a) peptide (VGSQIPEKMQKHPWRQVCDRGI).

SEQ ID NO:44 is a SSX-5$_{13-34}$ (isoform b) peptide (VGSQIPEKMQKAFDDIAKYFSE).

SEQ ID NO:45 is a SSX-6$_{13-34}$ peptide (DDAKASEKRSKAFDDIAKYFSK).

SEQ ID NO:46 is a SSX-7$_{13-34}$ peptide (AGAQIPEKIQKSFDDIAKYFSK).

SEQ ID NO:47 is a SSX-8$_{13-34}$ peptide (DDDKASEKRSKAFNDIATYFSK).

SEQ ID NO:48 is a SSX-9$_{13-34}$ peptide (AGSQIPEKIQKAFDDIAKYFSK).

DETAILED DESCRIPTION OF THE INVENTION

The invention provides isolated SSX-2 peptides presented by HLA class II molecules, which peptides stimulate the proliferation and activation of CD4$^+$ T lymphocytes. Such peptides are referred to herein as "SSX-2 HLA class II binding peptides," "HLA class II binding peptides" and "MHC class II binding peptides." Hence, one aspect of the invention is an isolated peptide which includes the amino acid sequence of SEQ ID NO:8, preferably any one of SEQ ID NOs: 1-7. The peptides referred to herein as "SSX-2 HLA class II binding peptides" include fragments of SSX-2 protein, but do not include full-length SSX-2 protein (e.g., SEQ ID NOs:10, 12 or 14). Likewise, nucleic acids that encode the "SSX-2 HLA class to II binding peptides" include fragments of the SSX-2 gene coding region, but do not include the full-length SSX-2 coding region (e.g., as found in SEQ ID NOs: 9, 11 or 13).

The examples below show the isolation of peptides which are SSX-2 HLA class II binding peptides. These exemplary peptides are processed translation products of an SSX-2 nucleic acid (e.g., SEQ ID NOs:9, 11 and 13; the encoded polypeptide sequences are given as SEQ ID NOs:10, 12 and 14). As such, it will be appreciated by one of ordinary skill in the art that the translation products from which a SSX-2 HLA class II binding peptide is processed to a final form for presentation may be of any length or sequence so long as they encompass the SSX-2 HLA class II binding peptide. As demonstrated in the examples below, peptides or proteins as small as 14 amino acids and as large as the amino acid sequence of a SSX-2 protein (SEQ ID NOs:10, 12 and 14) are appropriately processed, presented by HLA class II molecules and effective in stimulating CD4$^+$ T lymphocytes. SSX-2 HLA class II binding peptides, such as the peptides of SEQ ID NO:1, SEQ ID NO:2, SEQ ID NO:3, SEQ ID NO:4, SEQ ID NO:5, SEQ ID NO:6 and SEQ ID NO:7 may have one, two, three, four, five, six, seven, eight, nine, ten, 15, 20, 25, 30, 40, 50 or more amino acids added to either or both ends. The antigenic portion of such a peptide is cleaved out under physiological conditions for presentation by HLA class II molecules. It is also well known in the art that HLA class II peptide length is variable between about 10 amino acids and about 30 amino acids (Engelhard, *Ann. Rev. Immunol.* 12:181-201, 1994). Most of the HLA class II binding peptides fall in to the length range of 12-19 amino acids. Nested sets of HLA class II binding peptides have been identified, wherein the peptides share a core sequence but have different amino acids at amino and/or carboxyl terminal ends (see, e.g., Chicz et al., *J. Exp. Med.* 178:27-47, 1993). Thus additional SSX-2 HLA class II binding peptides comprising at least a portion of the sequences of the peptides reported herein, preferably comprising SEQ ID NO:8, as well as homologous SSX family HLA class II binding peptides (e.g., of similar sequence from other SSX proteins including SSX-1, SSX-3 and SSX-4), can be identified by one of ordinary skill in the art according to the procedures described herein.

The procedures described in the Examples that were utilized to identify SSX-2 HLA class II binding peptides also can be utilized to identify other HLA class II binding peptides, including homologous SSX family HLA class II binding peptides. Thus, for example, one can load antigen presenting cells, such as dendritic cells of normal blood donors, with a to recombinant SSX protein (or a number of overlapping peptide fragments thereof as is described herein) by contacting the cells with the SSX polypeptide (or a series of peptides) or by introducing into the cells a nucleic acid molecule which directs the expression of the SSX protein (or peptide) of interest. The antigen-presenting cells then can be used to induce in vitro the activation and/or proliferation of specific CD4 lymphocytes that recognize SSX HLA class II binding peptides. The CD4 lymphocytes can be isolated according to standard methods, including cytokine guided flow cytometry cell sorting as described herein. The sequence of the peptide epitope then can be determined as described in the Examples, e.g., by stimulating cells with peptide fragments of the SSX protein used to stimulate the activation and/or proliferation of CD4 lymphocytes. If a peptide library is used in the initial screening, then subsets of these peptides or individual peptides can be used for the subsequent screening. Preferably the peptides are at least about 12 amino acids in length for efficient binding to HLA class II molecules. More preferably, the peptides are between about 14 and about 50 amino acids in length, still more preferably between about 20 and about 22 amino acids in length. By using overlapping peptides, all possible epitopes can be screened. In some embodiments, the peptides overlap each other by at least about 4 amino acids, but preferably the peptides overlap each other by at least about 10 amino acids. In addition, one can make predictions of peptide sequences derived from SSX family proteins which are candidate HLA class II binding peptides based on the consensus amino acid sequences for binding HLA class II molecules. Peptides which are thus selected can be used in the assays described herein for inducing activation and/or proliferation of specific CD4 lymphocytes and identification of peptides. Additional methods of selecting and testing peptides for HLA class II binding are well known in the art. The foregoing methods also can be used to simultaneously screen a protein sequence for the presence of both HLA class I and HLA class II epitopes by contacting the antigen presenting cells with a population of cells that contans both CD4$^+$ T lymphocytes and CD8$^+$ T lymphocytes. The stimulation of both CD4$^+$ and CD8$^+$ T lymphocytes indicates that a peptide in the synthetic library contains both HLA class I and HLA class II epitopes. Stimulation of CD8$^+$ or CD4$^+$ T lymphocytes indicates that only HLA class I or HLA class II epitopes exist in a reactive peptide.

As noted above, the invention embraces functional variants of SSX-2 HLA class II binding peptides. As used herein, a "functional variant" or "variant" of a HLA class II to binding peptide is a peptide which contains one or more modifications to the primary amino acid sequence of a HLA class II binding peptide and retains the HLA class II and T cell receptor binding properties disclosed herein. Modifications which create a SSX-2 HLA class II binding peptide functional variant can be made for example 1) to enhance a property of a SSX-2 HLA class II binding peptide, such as peptide stability in an expression system or the stability of protein-protein binding such as HLA-peptide binding; 2) to provide a novel activity or property to a SSX-2 HLA class II binding peptide, such as addition of an antigenic epitope or addition of a detectable moiety; or 3) to provide a different amino acid sequence that produces the same or similar T cell stimulatory properties. Modifications to SSX-2 (as well as SSX family) HLA class II binding peptides can be made to nucleic acids which encode the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Variants also can be selected from libraries of peptides, which can be random peptides or peptides based on the sequence of the SSX peptides including substitutions at one or more positions (preferably 1-5). For example, a peptide library can be used in competition assays with complexes of SSX peptides bound to HLA class II molecules (e.g. dendritic cells loaded with SSX peptide). Peptides which compete for binding of the SSX peptide to the HLA class II molecule can be sequenced and used in other assays (e.g. CD4 lymphocyte proliferation) to determine suitability as SSX peptide functional variants. Preferred functional variants include SEQ ID NOs:40-42 and SEQ ID NOs:44-48, as shown in Table III, and fragments thereof that bind HLA class II molecules.

Modifications also embrace fusion proteins comprising all or part of a SSX HLA class II binding peptide amino acid sequence, such as the invariant chain-SSX-2 fusion proteins described herein. The invention thus embraces fusion proteins comprising SSX-2 HLA class II binding peptides and endosomal targeting signals such as the human invariant chain (Ii). As is disclosed below, fusion of an endosomal targeting portion of the human invariant chain to SSX-2 resulted in efficient targeting of SSX-2 to the HLA class II peptide presentation pathway. An "endosomal targeting portion" of the human invariant chain or other targeting polypeptide is that portion of the molecule which, when fused or conjugated to a second to polypeptide, increases endosomal localization of the second polypeptide. Thus endosomal targeting portions can include the entire sequence or only a small portion of a targeting polypeptide such as human invariant chain Ii. One of ordinary skill in the art can readily determine an endosomal targeting portion of a targeting molecule.

Prior investigations (PCT/US99/21230) noted that fusion of an endosomal targeting portion of LAMP-1 protein did not significantly increase targeting of MAGE-A3 to the HLA class II peptide presentation pathway. It is possible that this was a MAGE-A3 specific effect. Therefore, the SSX-2 peptides of the invention can be tested as fusions with LAMP-1 to determine if such fusion proteins are efficiently targeted to the HLA class II peptide presentation pathway. Additional endosomal targeting signals can be identified by one of ordinary skill in the art, fused to SSX-2 or a SSX-2 HLA class II binding portion thereof, and tested for targeting to the HLA class II peptide presentation pathway using no more than routine experimentation.

The amino acid sequence of SSX HLA class II binding peptides may be of natural or non-natural origin, that is, they may comprise a natural SSX HLA class II binding peptide molecule or may comprise a modified sequence as long as the amino acid sequence retains the ability to stimulate helper T cells when presented and retains the property of binding to an HLA class II molecule such as an HLA DP molecule. For example, SSX-2 HLA class II binding peptides in this context may be fusion proteins including a SSX-2 HLA class II binding peptide and unrelated amino acid sequences, synthetic SSX-2 HLA class II binding peptides, labeled peptides, peptides isolated from patients with a SSX-2 expressing cancer, peptides isolated from cultured cells which express SSX-2, peptides coupled to nonpeptide molecules (for example in certain drug delivery systems) and other molecules which include the amino acid sequence of SEQ ID NOs:1-8.

Preferably, the SSX-2 HLA class II binding peptides are non-hydrolyzable. To provide such peptides, one may select SSX-2 HLA class II binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing CD4+ T lymphocytes and then modify such peptides as necessary to reduce the potential for hydrolysis by proteases. For example, to determine the susceptibility to proteolytic cleavage, peptides may to be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a SSX-2 HLA class II binding peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include, but are not limited to, -psi[$CH_2NH$]-reduced amide peptide bonds, -psi[$COCH_2$]-ketomethylene peptide bonds, -psi[CH(CN)NH]-(cyanomethylene)amino peptide bonds, -psi[$CH_2CH(OH)$]-hydroxyethylene peptide bonds, -psi[$CH_2O$]-peptide bonds, and -psi[$CH_2S$]-thiomethylene peptide bonds.

Nonpeptide analogs of peptides, e.g., those which provide a stabilized structure or lessened biodegradation, are also contemplated. Peptide mimetic analogs can be prepared based on a selected SSX-2 HLA class II binding peptide by replacement of one or more residues by nonpeptide moieties. Preferably, the nonpeptide moieties permit the peptide to retain its natural conformation, or stabilize a preferred, e.g., bioactive, confirmation. Such peptides can be tested in molecular or cell-based binding assays to assess the effect of the substitution(s) on conformation and/or activity. One example of methods for preparation of nonpeptide mimetic analogs from peptides is described in Nachman et al., *Regul. Pept.* 57:359-370 (1995). Peptide as used herein embraces all of the foregoing.

If a variant involves a change to an amino acid of SEQ ID NOs:1-8, functional variants of the SSX-2 HLA class II binding peptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the SSX-2 HLA class II binding peptides are provided in a published PCT application of Strominger and Wucherpfennig (PCT/US96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Other computational methods for selecting amino acid substitutions, such as iterative computer structural modeling, can also be performed by one of ordinary skill in the art to prepare variants. Sequence motifs for SSX-2 HLA class II binding peptide functional variants can be developed by analysis of the binding domains or binding pockets of major histocompatibility complex HLA-DP proteins and/or the T cell receptor ("TCR") contact points of the SSX-2 HLA class II binding peptides disclosed herein. By providing a detailed structural analysis of the residues involved in forming the HLA class II binding pockets, one is enabled to make predictions of sequence motifs for binding of SSX peptides to any of the HLA class II proteins.

Using these sequence motifs as search, evaluation, or design criteria, one is enabled to identify classes of peptides (e.g. SSX HLA class II binding peptides, particularly the SSX-2 peptides disclosed herein, and functional variants thereof) which have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference, describe the HLA class II and TCR binding pockets which contact residues of an HLA class II peptide. By keeping the residues which are likely to bind in the HLA class II and/or TCR binding pockets constant or permitting only specified substitutions, functional variants of SSX HLA class II binding peptides can be prepared which retain binding to HLA class II and T cell receptor.

Thus methods for identifying additional SSX family HLA class II peptides, in particular SSX-2 HLA class II binding peptides, and functional variants thereof, are provided. In general, any SSX protein can be subjected to the analysis noted above, peptide sequences selected and the tested as described herein. With respect to SSX-2, for example, the methods include selecting a SSX-2 HLA class II binding peptide, an HLA class II binding molecule which binds the SSX-2 HLA class II binding peptide, and a T cell which is stimulated by the SSX-2 HLA class II binding peptide presented by the HLA class II binding molecule. In preferred embodiments, the SSX-2 HLA class II binding peptide comprises the amino acid sequence of SEQ ID NOs:1-8. More preferably, the peptide consists essentially of or consists of the amino acid sequences of SEQ ID NOs:1-7. The first amino acid residue of the SSX-2 HLA class II binding peptide is mutated to prepare a variant peptide. The amino acid residue can be mutated according to the principles of HLA and T cell receptor contact points set forth in the Strominger and Wucherpfennig PCT application described above. Any method for preparing variant peptides can be employed, such as synthesis of the variant peptide, recombinantly producing the variant peptide using a mutated nucleic acid molecule, and the like.

The binding of the variant peptide to HLA class II binding molecules and stimulation of the T cell are then determined according to standard procedures. For example, as exemplified below, the variant peptide can be contacted with an antigen presenting cell which contains the HLA class II molecule which binds the SSX-2 peptide to form a complex of the variant peptide and antigen presenting cell. This complex can then be contacted with a T cell which recognizes the SSX-2 HLA class II binding peptide presented by the HLA class II binding molecule. T cells can be obtained from a patient having a condition characterized by expression of SSX-2, such as cancer. Recognition of variant peptides by the T cells can be determined by measuring an indicator of T cell stimulation such as cytokine production (e.g., TNF or IFN-γ) or proliferation of the T cells. Similar procedures can be carried out for identification and characterization of other SSX family HLA class II binding peptides.

Binding of a variant peptide to the HLA class II binding molecule and stimulation of the T cell by the variant peptide presented by the HLA class II binding molecule indicates that the variant peptide is a functional variant. The methods also can include the step of comparing the stimulation of the T cell by the SSX-2 HLA class II binding peptide and the stimulation of the T cell by the functional variant as a determination of the effectiveness of the stimulation of the T cell by the functional variant. By comparing the functional variant with the SSX-2 HLA class II binding peptide, peptides with increased T cell stimulatory properties can be prepared.

The foregoing methods can be repeated sequentially with a second, third, fourth, fifth, sixth, seventh, eighth, ninth, and tenth substitutions to prepare additional functional variants of the disclosed SSX-2 HLA class II binding peptides.

Variants of the SSX-2 HLA class II binding peptides prepared by any of the foregoing methods can be sequenced, if necessary, to determine the amino acid sequence and thus deduce the nucleotide sequence which encodes such variants.

Also a part of the invention are those nucleic acid sequences which code for a SSX HLA class II binding peptides or variants thereof and other nucleic acid sequences which hybridize to a nucleic acid molecule consisting of the above described nucleotide sequences, under high stringency conditions. Preferred nucleic acid molecules include those comprising the nucleotide sequences that encode SEQ ID NOs:1-7, which are SEQ ID NOs:15-21, respectively. The term "stringent conditions" as used herein refers to parameters with which the art is familiar Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high stringency conditions, as used herein, refers to hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH7), 0.5% SDS, 2 mM EDTA). SSC is 0.15M Sodium Chloride/0.015M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1-0.5×SSC/0.1×SDS at temperatures up to 68° C. Alternatively, high stringency to hybridization may be performed using a commercially available hybridization buffer, such as ExpressHyb™ buffer (Clontech) using hybridization and washing conditions described by the manufacturer.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the SSX HLA class II binding peptides of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity and/or at least 90% amino acid identity to the nucleic acids that encode a SSX-2 HLA class II binding peptide (such as SEQ ID NOs:1-7) or to the amino acid sequence of such a peptide, respectively. In some instances homologs and alleles will share at least 90% nucleotide identity and/or at least 95% amino acid identity, in other embodiments homologs and alleles will share at least 95% nucleotide identity and/or at least 98% amino acid identity, in further embodiments homologs and alleles will share at least 97% nucleotide identity and/or at least 99% amino acid identity and in still other instances will share at least 99% nucleotide identity and/or at least 99.5% amino acid identity. Complements of the foregoing nucleic acids also are embraced by the invention.

In screening for nucleic acids which encode a SSX HLA class II binding peptide, a nucleic acid hybridization such as a Southern blot or a Northern blot may be performed using the foregoing conditions, together with a detectably labeled probe (e.g., radioactive such as $^{32}P$, chemiluminescent, fluorescent labels). After washing the membrane to which DNA encoding a SSX HLA class II binding peptide was finally transferred, the membrane can be placed against X-ray film, phosphorimager or other detection device to detect the detectable label.

The invention also includes the use of nucleic acid sequences which include alternative codons that encode the same amino acid residues of the SSX HLA class II binding peptides. For example, as disclosed herein, the peptide VGA-QIPEKIQKAFDDIAKYFSK (SEQ ID NO:1) is a SSX-2 HLA class II binding peptide. The lysine residues (amino acids No. 8, 11, 18, and 22 of SEQ ID NO:1) can be encoded by the codons AAA, and AAG. Each of the two codons is equivalent for the purposes of encoding a lysine residue. Thus, it will be apparent to one of ordinary skill in the art that any of the lysine-encoding nucleotide triplets may be employed to direct the protein synthesis apparatus, in vitro or in vivo, to incorporate a lysine residue. Similarly, nucleotide sequence triplets which encode other amino acid residues comprising the SSX-2 HLA class II binding peptide of SEQ ID NO:1 include: GUA, GUC, GUG and GUU (valine codons); GAA and GAG (glutamine codons); UUC and UUU (phenylalanine codons) and UAC and UAU (tyrosine codons). Other amino acid residues may be encoded similarly by multiple nucleotide sequences. Thus, the invention embraces degenerate nucleic acids that differ from the native SSX HLA class II binding peptide encoding nucleic acids in codon sequence due to the degeneracy of the genetic code.

It will also be understood that the invention embraces the use of the sequences in expression vectors, as well as to transfect host cells and cell lines, be these prokaryotic (e.g., *E. coli*), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. As it has been found that human HLA-DP molecules present a SSX-2 HLA class II binding peptide, the expression vector may also include a nucleic acid sequence coding for an HLA-DP molecule. In a situation where the vector contains both coding sequences, it can be used to transfect a cell which does not normally express either one. The SSX-2 HLA class II binding peptide coding sequence may be used alone, when, e.g. the host cell already expresses an HLA-DP molecule. Of course, there is no limit on the particular host cell which can be used as the vectors which contain the two coding sequences may be used in host cells which do not express HLA-DP molecules if desired, and the nucleic acid coding for the SSX-2 HLA class II binding peptide can be used in antigen presenting cells which express an HLA-DP molecule.

As used herein, "an HLA-DP molecule" includes the preferred subtypes DP101 and DP301 (i.e., DPB1*0101 AND DPB1*0301, including alleles DPB1*010101, DPB1*010102, DPB1*030101 and DPB1*030102), and other subtypes known to one of ordinary skill in the art. Other subtypes, including those related to DP101 and DP301 can be found in various to publications and internet resources that update HLA allele lists.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or after integration into the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

Preferably the expression vectors contain sequences which target a SSX family polypeptide, e.g. SSX-2, or a HLA class II binding peptide derived therefrom, to the endosomes of a cell in which the protein or peptide is expressed. HLA class II molecules contain an invariant chain (Ii) which impedes binding of other molecules to the HLA class II molecules. This invariant chain is cleaved in endosomes, thereby permitting binding of peptides by HLA class II molecules. Therefore it is preferable that the SSX-2 HLA class II to binding peptides and precursors thereof (e.g. the SSX-2 protein) are targeted to the endosome, thereby enhancing the binding of SSX-2 HLA class II binding peptide to HLA class II molecules. Targeting signals for directing molecules to endosomes are known in the art and these signals conveniently can be incorporated in expression vectors such that fusion proteins which contain the endosomal targeting signal are produced. Sanderson et al. (*Proc. Nat'l. Acad. Sci. USA* 92:7217-7221, 1995), Wu et al. (*Proc. Nat'l. Acad. Sci. USA* 92:11671-11675, 1995) and Thomson et al (*J. Virol.* 72:2246-2252, 1998) describe endosomal targeting signals (including invariant chain Ii and lysosomal-associated membrane protein LAMP-1) and their use in directing antigens to endosomal and/or lysosomal cellular compartments.

Endosomal targeting signals such as invariant chain also can be conjugated to SSX-2 protein or peptides by non-peptide bonds (i.e. not fusion proteins) to prepare a conjugate capable of specifically targeting SSX-2. Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available cross-linkers are reactive with one or more of the following groups; primary amines, secondary amines, sulfhydryls, carboxyls, carbonyls and carbohydrates. One of ordinary skill in the art will be able to ascertain without undue experimentation the preferred molecule for linking the endosomal targeting moiety and SSX-2 peptide or protein, based on the chemical properties of the molecules being linked and the preferred characteristics of the bond or bonds.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the to transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a SSX-2 HLA class II binding peptide. That heterologous DNA (RNA) is placed under operable control of transcriptional elements to permit the expression of the heterologous DNA in the host cell. As described herein, such expression constructs optionally also contain nucleotide sequences which encode endosomal targeting signals, preferably human invariant chain or a targeting fragment thereof Preferred systems for mRNA expression in mammalian cells are those such as pRc/CMV and pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is disclosed by Warnier et al., in intradermal injection in mice for immunization against P1A (*Int. J. Cancer,* 67:303-310, 1996). Recombinant vectors including viruses selected from the group consisting of adenoviruses, adeno-associated viruses, poxviruses including vaccinia viruses and attenuated poxviruses such as ALVAC, NYVAC, Semliki Forest virus, Venezuelan equine encephalitis virus, retroviruses, Sindbis virus, Ty virus-like particle, other alphaviruses, VSV, plasmids (e.g. "naked" DNA), bacteria (e.g. the bacterium Bacille Calmette Guerin, attenuated *Salmonella*), and the like can be used in such delivery, for example, for use as a vaccine.

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. The following uses are described for SSX-2 HLA class II binding peptides but are equally applicable to use of other SSX family HLA class II binding peptides. First, the invention permits the artisan to diagnose a disorder characterized by expression of a SSX-2 HLA class II binding peptide. These methods involve determining expression or presence in a biological sample of a SSX-2 HLA class II binding peptide, or a complex of a SSX-2 HLA class II binding peptide and an HLA class II molecule. The expression of a peptide or complex of peptide and HLA class II molecule can be determined by assaying with a binding partner for the peptide or complex, such as an antibody, a T lymphocyte, a multimeric complex of T cell receptors specific for the complex, and the like. Assays that are well known in the immunological arts can be employed, such as ELISA, ELISPOT, flow cytometry, and the like.

The invention further includes nucleic acid or protein microarrays with components to that bind SSX-2 HLA class II peptides or nucleic acids encoding such polypeptides. In this aspect of the invention, standard techniques of microarray technology are utilized to assess expression of the SSX-2 polypeptides and/or identify biological constituents that bind such polypeptides. The constituents of biological samples include antibodies, lymphocytes (particularly T lymphocytes), T cell receptor molecules and the like. Protein microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485): 1760-1763, 2000. Nucleic acid arrays, particularly arrays that bind SSX-2 peptides also can be used for diagnostic applications, such as for identifying subjects that have a condition characterized by SSX-2 polypeptide expression.

Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate.

Targets are peptides or proteins and may be natural or synthetic. The tissue may be obtained from a subject or may be grown in culture (e.g. from a cell line).

In some embodiments of the invention one or more control peptide or protein molecules are attached to the substrate. Preferably, control peptide or protein molecules allow determination of factors such as peptide or protein quality and binding characteristics, reagent quality and effectiveness, binding success, and analysis thresholds and success.

Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol. 21, January 1999, the entire contents of which is incorporated by reference herein.

According to the present invention, nucleic acid microarray substrates may include but are not limited to glass, silica, aluminosilicates, borosilicates, metal oxides such as alumina and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of two or more molecule that bind the nucleic acid molecules that encode the SSX-2 HLA class II binding peptides set forth herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These to agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium. In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezoelectric delivery. Probes may be covalently linked to the substrate with methods that include, but are not limited to, UV-irradiation. In another embodiment probes are linked to the substrate with heat.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

The invention also permits the artisan to treat a subject having a disorder characterized by expression of a SSX-2 HLA class II binding peptide. Treatments include administering an agent which enriches in the subject a complex of a SSX-2 HLA class II binding peptide and an HLA class II molecule, and administering $CD4^+$ T lymphocytes which are specific for such complexes. Agents useful in the foregoing treatments include SSX-2 HLA class II binding peptides and functional variants thereof, proteins including such SSX-2 HLA class II binding peptides, optionally containing endosome targeting sequences fused to the SSX-2 sequences, nucleic acids which express such proteins and peptides (including viruses and other vectors that contain the nucleic acids), complexes of such peptides and HLA class II binding molecules (e.g., HLA DP), antigen presenting cells bearing complexes of a SSX-2 HLA class II binding peptide and an HLA class II binding molecule (such as dendritic cells bearing one or more SSX-2 HLA class II binding peptides bound to HLA class II molecules), and the like. The invention also permits an artisan to selectively enrich a population of T lymphocytes for $CD4^+$ T lymphocytes specific for a SSX-2 HLA class II binding peptide.

The isolation of the SSX-2 HLA class II binding peptides also makes it possible to isolate and/or synthesize nucleic acids that encode the SSX-2 HLA class II binding peptides. Nucleic acids can be used to produce in vitro or in prokaryotic or eukaryotic host cells the SSX-2 HLA class II binding peptides.

Peptides comprising the SSX-2 HLA class II binding peptide of the invention may be synthesized in vitro, using standard methods of peptide synthesis, preferably automated peptide synthesis. In additiona, a variety of other methodologies well-known to the skilled practitioner can be utilized to obtain isolated SSX-2 HLA class II binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Those skilled in the art also can readily follow known methods for isolating peptides in order to obtain isolated SSX-2 HLA class II binding peptides. These include, but are not limited to, immunochromatography, HPLC, size-exclusion chromatography, ion-exchange chromatography and immune-affinity chromatography.

These isolated SSX-2 HLA class II binding peptides, proteins which include such peptides, or complexes of the peptides and HLA class II molecules, such as HLA-DP, may be combined with materials such as adjuvants to produce vaccines useful in treating disorders characterized by expression of the SSX-2 HLA class II binding peptide. Preferably, vaccines are prepared from antigen presenting cells that present the SSX-2 HLA class II binding peptide/HLA class II complexes on their surface, such as dendritic cells, B cells, non-proliferative transfectants, etcetera. In all cases where cells are used as a vaccine, these can be cells transfected with coding sequences for one or both of the components necessary to stimulate $CD4^+$ lymphocytes, or be cells which already express both molecules without the need for transfection. For example, autologous antigen presenting cells can be isolated from a patient and treated to obtain cells which present SSX-2 epitopes in association of HLA class I and HLA class II molecules. These cells would be capable of stimulating both $CD4^+$ and $CD8^+$ cell responses. Such antigen presenting cells can be obtained by infecting dendritic cells with recombinant viruses encoding an Ii.SSX-2 fusion protein. Dendritic cells also can be loaded with HLA class I and HLA class II peptide epitopes.

Vaccines also encompass naked DNA or RNA, encoding a SSX-2 HLA class II binding peptide or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745-1748, 1993). Vaccines also include nucleic acids packaged in a virus, liposome or other particle, including polymeric particles useful in drug delivery.

The immune response generated or enhanced by any of the treatments described herein can be monitored by various methods known in the art. For example, the presence of T cells specific for a SSX-2 antigen can be detected by direct labeling of T cell receptors with soluble fluorogenic MHC molecule tetramers which present the antigenic SSX-2 peptide (Altman et al., *Science* 274:94-96, 1996; Dunbar et al., *Curr. Biol.* 8:413-416, 1998). Briefly, soluble MHC class I molecules are folded in vitro in the presence of $\beta$2-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio of 4:1. to Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein. The use of MHC class II molecules as tetramers was recently demonstrated by Crawford et al. (*Immunity* 8:675-682, 1998; see also Dunbar and Ogg, *J. Immunol. Methods* 268(1):3-7, 2002; Arnold et al., *J. Immunol. Methods* 271(1-2):137-151, 2002). Multimeric soluble MHC class II molecules were complexed with a covalently attached peptide (which can be attached with or without a linker molecule), but peptides also can be loaded onto class II molecules. The class II tetramers were shown to bind with appropriate specificity and affinity to specific T cells. Thus tetramers can be used to monitor both $CD4^+$ and $CD8^+$ cell responses to vaccination protocols. Methods for preparation of multimeric complexes of MHC class II molecules are described in Hugues et al., *J. Immunological Meth.* 268: 83-92, (2002) and references cited therein, each of which is incorporated by reference.

The SSX-2 HLA class II binding peptide, as well as complexes of SSX-2 HLA class II binding peptide and HLA molecule, also may be used to produce antibodies, using standard techniques well known to the art. Standard reference works setting forth the general principles of antibody production include Catty, D., *Antibodies, A Practical Approach*, Vol. 1, IRL Press, Washington D.C. (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N., *Microbiology*, third edition, Davis, B. D. et al. EDS. (Harper & Rowe, Philadelphia (1980).

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has to been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816, 567, 5,225,539, 5,585,089, 5,693,762 and 5,859,205.

Fully human monoclonal antibodies also can be prepared by immunizing mice transgenic for large portions of human immunoglobulin heavy and light chain loci. See, e.g., U.S. Pat. Nos. 5,545,806, 6,150,584, and references cited therein. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The antibodies of the present invention thus are prepared by any of a variety of methods, including administering protein, fragments of protein, cells expressing the protein or fragments thereof and an appropriate HLA class II molecule, and the like to an animal to induce polyclonal antibodies. The production of monoclonal antibodies is according to techniques well known in the art. Antibodies prepared according to the invention also preferably are specific for the peptide/HLA complexes described herein.

The antibodies of this invention can be used for experimental purposes (e.g., localization of the HLA/peptide complexes, immunoprecipitations, Western blots, flow cytometry, ELISA etc.) as well as diagnostic or therapeutic purposes (e.g., assaying extracts of tissue biopsies for the presence of the SSX-2 peptides, HLA/peptide complexes, targeting delivery of cytotoxic or cytostatic substances to cells expressing the appropriate HLA/peptide complex). The antibodies of this invention are useful for the study and analysis of antigen presentation on tumor cells and can be used to assay for changes in the HLA/peptide complex expression before, during or after a treatment protocol, e.g., vaccination with peptides, antigen presenting cells, HLA/peptide tetramers, adoptive transfer or chemotherapy.

The antibodies and antibody fragments of this invention may be coupled to diagnostic labeling agents for imaging of cells and tissues that express the HLA/peptide complexes or may be coupled to therapeutically useful agents by using standard methods well-known in the art. The antibodies also may be coupled to labeling agents for imaging e.g., radiolabels or fluorescent labels, or may be coupled to, e.g., biotin or antitumor agents, e.g., radioiodinated compounds, toxins such as ricin, methotrexate, cytostatic or cytolytic drugs, etc. Examples of diagnostic agents suitable for conjugating to the antibodies of this invention include e.g., to barium sulfate, diatrizoate sodium, diatrizoate meglumine, iocetamic acid, iopanoic acid, ipodate calcium, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. As used herein, "therapeutically useful agents" include any therapeutic molecules, which are preferably targeted selectively to a cell expressing the HLA/peptide complexes, including antineoplastic agents, radioiodinated compounds, toxins, other cytostatic or cytolytic drugs. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-.alpha., lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or Pseudomonas exotoxin. Toxin moieties can also be high energy-emitting radionuclides such as cobalt-60. The antibodies may be administered to a subject having a pathological condition characterized by the presentation of the HLA/peptide complexes of this invention, e.g., melanoma or other cancers, in an amount sufficient to alleviate the symptoms associated with the pathological condition.

When "disorder" or "condition" is used herein, it refers to any pathological condition where the SSX-2 HLA class II binding peptide is expressed. Such disorders include cancers, such as biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; to lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms tumor.

Some therapeutic approaches based upon the disclosure are premised on inducing a response by a subject's immune system to SSX HLA class II binding peptide presenting cells. One such approach is the administration of autologous $CD4^+$ T cells specific to the complex of SSX-2 HLA class II binding peptide and an HLA class II molecule to a subject with abnormal cells of the phenotype at issue. It is within the skill of the artisan to develop such $CD4^+$ T cells in vitro. Generally, a sample of cells taken from a subject, such as blood cells, are contacted with a cell presenting the complex and capable of provoking $CD4^+$ T lymphocytes to proliferate. The target cell can be a transfectant, such as a COS cell, or an antigen presenting cell bearing HLA class II molecules, such as dendritic cells or B cells. These transfectants present the desired complex of their surface and, when combined with a $CD4^+$ T lymphocyte of interest, stimulate its proliferation. COS cells are widely available, as are other suitable host cells. Specific production of $CD4^+$ T lymphocytes is described below. The clonally expanded autologous $CD4^+$ T lymphocytes then are administered to the subject. The $CD4^+$ T lymphocytes then stimulate the subject's immune response, thereby achieving the desired therapeutic goal.

CTL proliferation can be increased by increasing the level of tryptophan in T cell cultures, by inhibiting enzymes which catabolizes tryptophan, such as indoleamine 2,3-dioxygenase (MO), or by adding tryptophan to the culture (see, e.g., PCT application WO99/29310). Proliferation of T cells is enhanced by increasing the rate of proliferation and/or extending the number of divisions of the T cells in culture. In addition, increasing tryptophan in T cell cultures also enhances the lytic activity of the T cells grown in culture.

The foregoing therapy assumes that at least some of the subject's abnormal cells present the relevant HLA/peptide complex. This can be determined very easily, as the art is very familiar with methods for identifying cells which present a particular HLA molecule, as well as how to identify cells expressing DNA of the pertinent sequences, in this case a SSX-2 sequence.

The foregoing therapy is not the only form of therapy that is available in accordance with the invention. CD4+ T lymphocytes can also be provoked in vivo, using a number of approaches. One approach is the use of non-proliferative cells expressing the complex. The cells used in this approach may be those that normally express the complex, such as dendritic cells or cells transfected with one or both of the genes necessary for presentation of the complex. Chen et al., (*Proc. Natl. Acad. Sci. USA* 88: 110-114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a SSX-2 HLA class II binding peptide may be operably linked to promoter and enhancer sequences which direct expression of the SSX-2 HLA class II binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding SSX-2 HLA class II binding peptides. Nucleic acids encoding a SSX-2 HLA class II binding peptide also may be inserted into a retroviral genome, thereby facilitating integration of the nucleic acid into the genome of the target tissue or cell type. In these systems, the gene of interest is carried by a microorganism, e.g., a Vaccinia virus, poxviruses in general, adenovirus, herpes simplex virus, retrovirus or the bacteria BCG, and the materials de facto "infect" host cells. The cells which result present the complex of interest, and are recognized by autologous CD4+ T cells, which then proliferate.

A similar effect can be achieved by combining a SSX HLA class II binding peptide with an adjuvant to facilitate incorporation into HLA class II presenting cells in vivo. If larger than the HLA class II binding portion (e.g., SEQ ID NOs:1-7), the SSX-2 HLA class II binding peptide can be processed if necessary to yield the peptide partner of the HLA molecule while the peptides disclosed herein are believed to be presented without the need for further processing. Generally, subjects can receive an intradermal injection of an effective amount of the SSX-2 HLA class II binding peptide. Initial doses can be followed by booster doses, following immunization protocols standard in the art.

A preferred method for facilitating incorporation of SSX-2 HLA class II binding peptides into HLA class II presenting cells is by expressing in the presenting cells a polypeptide which includes an endosomal targeting signal fused to a SSX-2 polypeptide which includes the class II binding peptide. Particularly preferred are SSX-2 fusion proteins which contain human invariant chain Ii.

Any of the foregoing compositions or protocols can include also SSX HLA class I binding peptides for induction of a cytolytic T lymphocyte response. For example, the SSX-2 protein can be processed in a cell to produce both HLA class I and HLA class II responses. SSX-2 peptides have been described in U.S. Pat. No. 6,548,064, and by Ayyoub et al. (*J Immunol* 168(4):1717-22, 2002) and Rubio-Godoy et al. (*Eur J Immunol.* 32:2292-2299, 2002). SSX gene and protein family members are disclosed in U.S. Pat. Nos. 6,291,658 and 6,339,140. By administering SSX-2 peptides which bind HLA class I and class II molecules (or nucleic acid encoding such peptides), an improved immune response may be provided by inducing both T helper cells and cytotoxic T cells.

In addition, non-SSX-2 tumor associated peptides also can be administered to increase immune response via HLA class I and/or class II. It is well established that cancer cells can express more that one tumor associated gene. It is within the scope of routine experimentation for one of ordinary skill in the art to determine whether a particular subject expresses additional tumor associated genes, and then include HLA class I and/or HLA class II binding peptides derived from expression products of such genes in the foregoing SSX-2 compositions and vaccines.

Especially preferred are nucleic acids encoding a series of epitopes, known as "polytopes". The epitopes can be arranged in sequential or overlapping fashion (see, e.g., Thomson et al., *Proc. Natl. Acad. Sci. USA* 92:5845-5849, 1995; Gilbert et al., *Nature Biotechnol.* 15:1280-1284, 1997), with or without the natural flanking sequences, and can be separated by unrelated linker sequences if desired. The polytope is processed to generated individual epitopes which are recognized by the immune system for generation of immune responses.

Thus, for example, SSX-2 HLA class II binding peptides can be combined with peptides from other tumor rejection antigens (e.g. by preparation of hybrid nucleic acids or polypeptides) and with SSX-2 HLA class I binding peptides (some of which are listed below) to form "polytopes". Exemplary tumor associated peptide antigens that can be administered to induce or enhance an immune response are derived from tumor associated genes and encoded proteins including MAGE-A1, MAGE-A2, MAGE-2, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-3, SSX-4, SSX-5, SCP-1 and CT-7. For example, antigenic peptides characteristic of tumors include those listed in published PCT application WO 00/20581 (PCT/US99/21230).

Other examples of HLA class I and HLA class II binding peptides will be known to one of ordinary skill in the art (for example, see Coulie, *Stem Cells* 13:393-403, 1995), and can be used in the invention in a like manner as those disclosed herein. One of ordinary skill in the art can prepare polypeptides comprising one or more SSX-2 peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci USA* 92(13):5845-5849, 1995; Gilbert et al., *Nature Biotechnol.* 15(12):1280-1284, 1997; Thomson et al., *J. Immunol.* 157(2):822-826, 1996; Tam et al., *J. Exp. Med.* 171(1):299-306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951-1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

As part of the immunization compositions, one or more substances that potentiate an immune response are administered along with the peptides described herein. Such substances include adjuvants and cytokines. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., *Mol. Cells* 7:178-186, 1997); incomplete Freund's adjuvant; complete Freund's adjuvant; montanide; immunostimulatory oligonucleotides (see e.g. CpG oligonucleotides described by Kreig et al., *Nature* 374:546-9, 1995); reagents that bind to one of the toll-like receptors; vitamin E and various water-in-oil emulsions prepared from biodegradable oils such as squalene and/or tocopherol. Preferably, the peptides are to administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 µg to about 100 µg. Other adjuvants are known in the art and can be used in the invention (see, e.g. Goding, *Monoclonal Antibodies: Principles and Practice,* 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432-1434, 1995), GM-CSF and IL-18. Thus cytokines can be administered in conjunction with antigens and adjuvants to increase the immune response to the antigens. There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation, and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284-6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637-5648, 1995). Tumor cell transfection with B7 has been discussed in relation to in vitro CTL expansion for adoptive transfer immunotherapy by Wang et al. (*J. Immunother.* 19:1-8, 1996). Other delivery mechanisms for the B7 molecule would include nucleic acid (naked DNA) immunization (Kim et al., *Nature Biotechnol.* 15:7:641-646, 1997) and recombinant viruses such as adeno and pox (Wendtner et al., *Gene Ther.* 4:726-735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., *Nature* 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.,* 158:637-642, 1997; Fenton et al., *J. Immunother.,* 21:95-108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art. In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the SSX-2 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to to those of ordinary skill in the art and can be addressed with no more than routine experimentation.

EXAMPLES

Because of its expression in different tumor types, the cancer/testis antigen SSX-2 is among the most promising candidates for the development of generic cancer vaccines. SSX-2 is a classical cancer testis antigen belonging to a multigene family mapping to chromosome X. Some family members, including SSX-2, are expressed in a wide variety of tumors (Naka et al. *Int J Cancer* 2002. 98:640-642). The SSX-2 encoding gene was initially described as one of two partner genes found in a recurrent chromosomal translocation in synovial sarcoma (Clark et al. *Nat Genet.* 1994. 7:502-508; Crew et al. *EMBO J.* 1995. 14:2333-2340), and more recently identified by SEREX analysis of serum from a melanoma patient. The potential spontaneous immunogenicity of the SSX-2 antigen was initially suggested by detection of specific antibodies in 10% of melanoma patients (Tureci et al, *Cancer Res* 1996. 56:4766-4772). By analyzing $CD8^+$ T lymphocytes from an SSX-2 expressing melanoma patient, an epitope was identified mapping to the 41-49 region of the SSX-2 protein and recognized by tumor-reactive $CD8^+$ T lymphocytes in association with the MHC Class I allele HLA-A2 (Rubio-Godoy et al., *Eur J Immunol.* 32:2292-2299, 2002; Ayyoub et al. *J Immunol* 168:1717-1722, 2002) Importantly, whereas a large functional avidity of antigen recognition and tumor reactivity has been found among isolated SSX2 41-49 specific $CD8^+$ T cells, those isolated from both tumor infiltrating and circulating lymphocytes of patients bearing SSX-2 expressing tumor lesions uniformly exhibited high functional avidity of antigen recognition and tumor reactivity. These findings indicate that spontaneous T cell responses to SSX-2 frequently occur in antigen expressing melanoma patients, encouraging the search for additional MHC class I and class II restricted epitopes in this patient population.

The first $CD4^+$ T cell epitope encoded by SSX-2 now has been identified, as described herein. The identified epitope mapped to the 19-34 region of the protein and was recognized by $CD4^+$ T cells from an antigen expressing melanoma patient in association with HLA-DP. The absence of detectable response in healthy donors and other patients suggests that SSX-2 specific $CD4^+$ T cells in the responder patient had been previously expanded in vivo in response to the autologous tumor. Interestingly, the epitope did not appear to be presented on the surface of tumor cells at levels sufficient to allow direct recognition. In contrast, it was efficiently presented by autologous dendritic cells, supporting the concept that processing by professional APC is the main pathway through which $CD4^+$ T cell immunoresponse to tumors antigens occurs in vivo.

Materials and Methods

Cell Lines and Tissue Culture.

Melanoma cell lines and anti HLA-DR (D1.12), HLA-DP (B7.21.3) and HLA-DQ (BT3/4) antibodies were kindly provided by Dr. D. Rimoldi (Ludwig Institute for Cancer Research, Lausanne, Switzerland). Cell lines were maintained in RPMI 1640 (Life Technologies, Gaithersburg, Md.) supplemented with 10% heat inactivated fetal calf serum (FCS). Culture medium for lymphocytes was IMDM (Life Technologies, Basel, Switzerland) supplemented with 8% heat inactivated pooled human serum (CTL medium), human recombinant IL-2 (Glaxo, Geneva, Switzerland) and IL-7 (Biosource International, Camarillo, Calif.).

Generation of SSX-2 Specific $CD4^+$ T Cells.

In vitro sensitization of $CD4^+$ T cells was carried out as described previously for $CD8^+$ T cells. Briefly, 1 to $2\times10^6$ $CD4^+$ T cells highly enriched from peripheral blood mononuclear cells (PBMC) by magnetic cell sorting using a mini-MACS device (Miltenyi Biotec, Sunnyvale, Calif., USA) were stimulated with a mixture containing peptides spanning the entire SSX-2 protein sequence (Ayyoub et al, *J Immunol* 2002. 32:2292-2299) (2 µM each) in the presence of irradiated autologous cells from the $CD4^-$ fraction in CTL medium containing rhIL-2 (10 U/ml) and IL-7 (10 pg/ml). The enriched $CD4^+$ T cells were cultured 2-3 weeks prior to being tested. $CD4^+$ T cells secreting cytokines in response to peptide stimulation were isolated by cytokine guided flow cytometry cell sorting using the cytokine secretion detection kit (Miltenyi Biotec) and cloned by limiting dilution culture in the presence of PHA (Sigma), allogenic irradiated PBMC and rhIL-2 as described (Valmori et al., 2001, *Cancer Res.*

61:501-512). Clones were subsequently expanded by periodic (3-4 weeks) stimulation under the same conditions.

Molecular typing of HLA-DP molecules, construction of plasmids and transient transfection. Primers pairs used for the PCR amplification of HLA-DP alleles were as follows: DPA forward primer: ATG CGC CCT GAA GAC AGA ATG T (SEQ ID NO:22); to DPA reverse primer: TCA CAG GGT CCC CTG GGC CCG GGG GA (SEQ ID NO:23); DPB forward primer: ATG ATG GTT CTG CAG GTT TCT G (SEQ ID NO:24); and DPB reverse primer: TTA TGC AGA TCC TCG TTG AAC TTT C (SEQ ID NO:25). Obtained sequences were searched against the IMGT-HLA database to confirm the HLA-DP identity (hosted at the European Bioinformatics Institute (EMBL-EBI) website). The SSX-2 plasmid contained the SSX-2 cDNA cloned into pcDNA3.1 vector. Tumor cells were transiently transfected with plasmids using FuGENE according to the manufacture's instructions (Roche Diagnostics, Rotkreuz, Switzerland).

Antigen Recognition Assays.

For intracellular cytokine secretion detection T cells were incubated with APC at a 1:1 T cells:APC ratio during 4-6 h in the absence or in the presence of peptides at the indicated dose. One hour after the beginning of the incubation Brefeldin A (20 µg/ml, Sigma Chemical Co., Steinheim, Germany) was added to inhibit cytokine secretion. At the end of the incubation period cells were stained with anti-CD4 mAb for 20 min at 4° C. and fixed. Cells were then permeabilized using saponine (Sigma, 0.1% in PBS 10% FCS) stained by incubation with mAb against IFN-γ or IL-2 (BD, Pharmingen) and analyzed by flow cytometry. Data analysis was performed using Cell Quest software. For detection of cytokine secretion in the culture supernatant T cells (10,000) were incubated with stimulating cells (15,000/well) in 96-well round-bottom plates in 200 µl/well of IMDM containing 10% human serum and 20 U/ml hrIL2. After 24 h incubation at 37° C., culture supernatants were collected and the content of IFN-γ determined by ELISA (BioSource Europe, Fleurus, Belgium). IFN-γ ELISPOT assay was performed as described previously (Ayyoub M. et al, 2002, *J Immunol* 32:2292-2299) using nitrocellulose-lined 96-well microplates (MAHA S45: Millipore, Bedford, Mass.) and an IFN-γ ELISPOT kit (DIACLONE, Besancon, France). Stimulator cells ($5 \times 10^4$/well) were added together with the indicated number of T cells and peptide (2 µM) where indicated. Spots were counted using a stereomicroscope with a magnification of ×15.

Results

Example 1

Assessment of SSX-2 Specific CD4+ T Cell Responses in Circulating Lymphocytes of Antigen Expressing Melanoma Patients Enriched CD4+ T cells from PBMC samples from 5 melanoma patients with detectable SSX-2 expression in their tumor lesions were stimulated in vitro with a peptide mix containing 15 20-22 amino acid long peptides spanning the SSX-2 protein sequence and overlapping by 10 amino acids (Ayyoub M. et al, 2002, *J Immunol* 32:2292-2299). Two to 3 weeks after a single in vitro stimulation, culture aliquots were stimulated with submixtures, each composed of 3 peptides; P1-3 was composed of the peptides as set forth in SEQ ID NO:26, SEQ ID NO:1, SEQ ID NO:27; P4-6 was composed of the peptides as set forth in SEQ ID NO:28, SEQ ID NO:29, SEQ ID NO:30; P7-9 was composed of the peptides as set forth in SEQ ID NO:31, SEQ ID NO:32, SEQ ID NO:33; P10-12 was composed of the peptides as set forth in SEQ ID NO:34, SEQ ID NO:35, SEQ ID NO:36; and P13-15 was composed of the peptides as set forth in SEQ ID NO:37, SEQ ID NO:38, SEQ ID NO:39. The presence of specific CD4+ T cells was monitored by intracellular staining with cytokine specific antibodies (IFN-γ, IL-2, FIG. 1 and Table I). For one patient (LAU 672), one peptide submixture (P1-3, containing peptides SEQ ID NO:26, SEQ ID NO:1 and SEQ ID NO:27) stimulated a significant proportion of IFN-γ and IL-2 secreting CD4+ T cells, as compared to controls containing either no peptide or other peptide mixtures (FIG. 1 and Table I). No specific responses were detected in the case of the other 4 melanoma patients analyzed (not shown). Assessment of reactivity of the culture from patient LAU 672 to single peptides in the submixture P1-3 (SEQ ID NO:26, SEQ ID NO:1, SEQ ID NO:27) revealed that SEQ ID NO:1 was the active peptide, whereas no significant activity was detected in response to peptides SEQ ID NO:22 and SEQ ID NO:23 (not shown). Peptide SSX-2 13-34 (SEQ ID NO:1) specific CD4+ T cells were isolated from the culture by cytokine secretion guided flow cytometry cell sorting and cloned under limiting dilution conditions. The obtained clonal populations were used for further experiments.

TABLE I

Data obtained for all peptide submixtures

| Peptides | % CD4+ IFN-γ+ | % CD4+ IL-2+ |
|---|---|---|
| None | 0.09 | 0.02 |
| SSX-2 P1-3: SEQ ID NO: 26, SEQ ID NO: 1, SEQ ID NO: 27 | 1.17 | 0.39 |
| SSX-2 P4-6: SEQ ID NO: 28, SEQ ID NO: 29, SEQ ID NO: 30 | 0.29 | 0.05 |
| SSX-2 P7-9: SEQ ID NO: 31, SEQ ID NO: 32, SEQ ID NO: 33 | 0.13 | 0.04 |
| SSX-2 P10-12: SEQ ID NO: 34, SEQ ID NO: 35, SEQ ID NO: 36 | 0.09 | 0.01 |
| SSX-2 P13-15: SEQ ID NO: 37, SEQ ID NO: 38, SEQ ID NO: 39 | 0.17 | 0.03 |

Example 2

Figure 2:
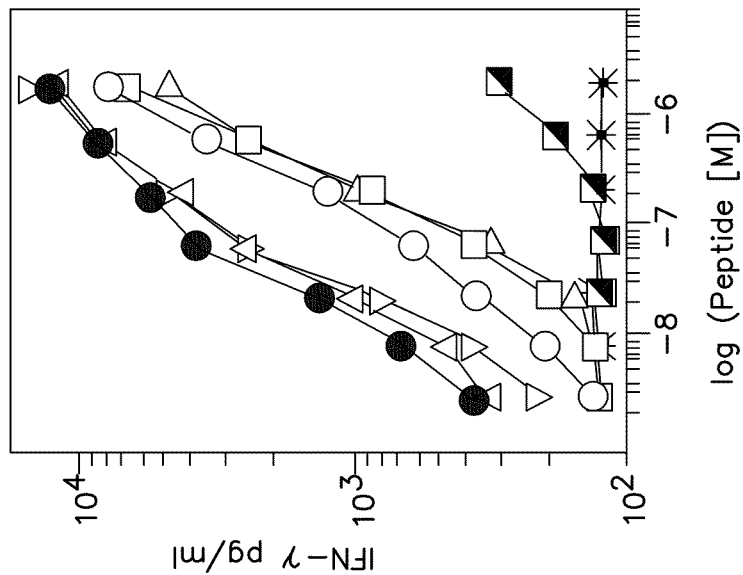
FIG. 2 depicts determination of the minimal sequence optimally recognized by SSX-2 specific CD4+ T cells. Synthetic peptides extended or truncated at the SSX-2$_{13-34}$ N- or C-terminus were used to determine the minimal length of the epitope recognized by SSX-2 specific CD4+ T cells. Serial dilutions of each peptide were incubated with EBV LAU 149 and SSX-2 specific CD4+ T cells. IFN-γ secretion was determined by ELISA in the culture supernatant after 24 hrs of culture. The peptides tested were: VGAQIPEKIQKAFDDI-AKYFSK (SSX-2$_{13-34}$; SEQ ID NO:1); VGAQIPEKIQKAF-DDIAKYFSKEE (SSX-2$_{13-36}$; SEQ ID NO:2); VGAQIPE-KIQKAFDDIAKYF (SSX-2$_{13-32}$; SEQ ID NO:3); VGAQIPEKIQKAFDDIAK (SSX-2$_{13-30}$; SEQ ID NO:4); IPEKIQKAFDDIAKYFSK (SSX-2$_{17-34}$; SEQ ID NO:5); EKIQKAFDDIAKYFSK (SSX-2$_{19-34}$; SEQ ID NO:6); IQKAFDDIAKYFSK (SSX-2$_{21-34}$; SEQ ID NO:7) and LGFKATLPPFMCNKRAEDFQGN (SSX-2$_{61-82}$; SEQ ID NO:30).

Mapping of the Minimal Peptide Optimally Recognized by SSX-2 Specific CD4+ T Cells To more precisely define the SSX-2-derived peptide optimally recognized by specific CD4+ T cells from patient LAU 672, we analyzed the relative capacity of peptide SEQ ID to NO:1 extended or truncated variants to stimulate IFN-γ secretion by specific clonal T cells (clone 2C3). As illustrated in FIG. 2, both extension and truncation of peptide SEQ ID NO:1 C-terminus resulted in decreased peptide recognition. Truncation of the first 6 amino acids at the N-terminus did not significantly affect recognition (SEQ ID NO:5 and SEQ ID NO:6). In contrast, truncation of 2 additional N-terminal amino acids resulted in a 10-fold reduction of peptide activity (SEQ ID NO:7). Thus, among analyzed peptides, SEQ ID NO:6 was the minimal peptide optimally recognized by SSX-2 specific CD4+ T cells, with SEQ ID NO:8 representing the core peptide sequence for peptides recognized by CD4+ T cells. Similar results were obtained using another CD4+ T cell clone (not shown).

Example 3

SSX-2 13-34 is Recognized by Specific CD4+ T Cells in the Context of HLA-DP101 and DP301

Figures 3A, 3B:
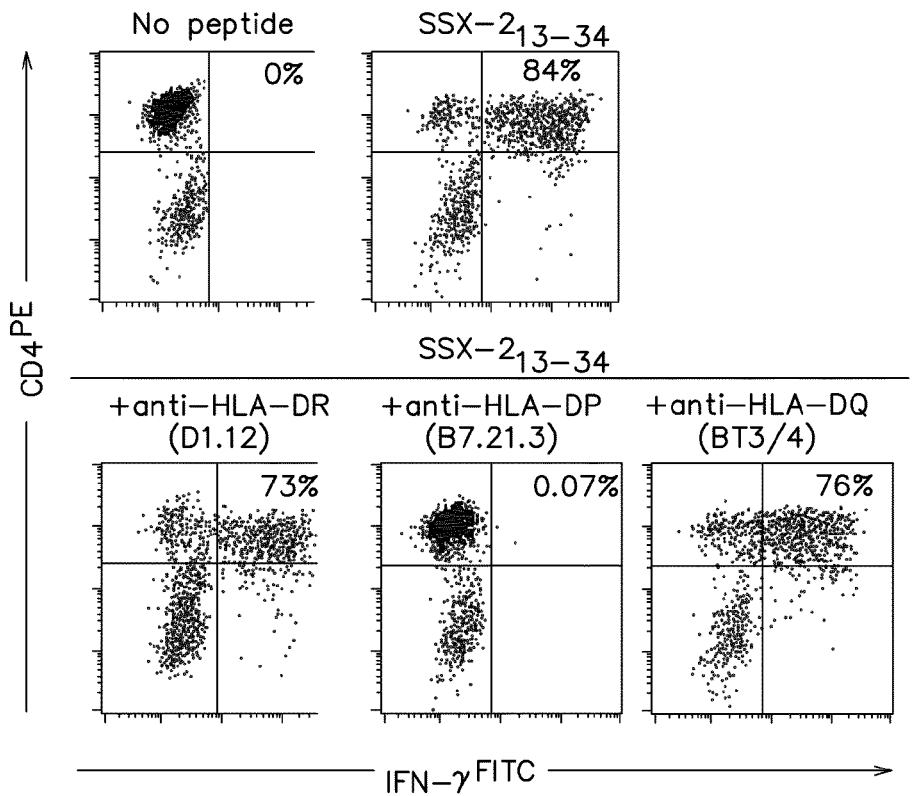
FIGS. 3A and 3B demonstrate recognition of SSX-2$_{13-34}$ by specific CD4+ T cells in the context of HLA-DP.

To identify the restriction element used by SSX-2 specific CD4+ T cells, recognition of peptide SSX-2 13-34 (SEQ ID NO:1) was carried out in the presence of antibodies that specifically block the recognition of antigens restricted by different MHC Class II elements (HLA-DR, HLA-DP or HLA-DQ). As illustrated in FIG. 3, anti-HLA-DP antibodies abolished the ability of SSX-2 specific CD4+ T cells to recognize peptide 13-34 (SEQ ID NO:1). In contrast, no significant inhibition was observed using anti HLA-DR or anti-HLA-DQ antibodies (FIG. 3). Under similar experimental conditions, no significant inhibition of recognition of peptide SSX-2 41-49 by specific CD8+ T cells was observed (not shown). To attempt establishing the HLA-DP presenting allele(s) we first analyzed the frequency at which PBMC from healthy donors were able to present the SSX-2 epitope to CD4+ T cells. We obtained presentation by 3 out of 14 PBMC analyzed suggesting a frequency of the presenting allele(s) in the test population (Caucasian) of about 20% (not shown). Presentation was to further assessed by using a series of HLA-DP typed APC including autologous APC from patient LAU 672 (Table II). Patient LAU 672 expressed HLA-DP101 and DP402. Peptide presentation in the context of the DP402, as well as DP401 (the more frequently expressed DP alleles) was excluded by the lack of presentation obtained with APC expressing the corresponding alleles. Thus, DP101 was the presenting allele in the case of patient LAU 672. In addition, peptide presentation was obtained using DP301/DP402 expressing APC indicating that the peptide can also be recognized by T cells in the context of the DP301 allele. The expression frequency of DP101 and DP301 (reported for the French population, (Charron D. et al., 1997, In *XIIth International Histocompatability Workshop and Conference*) is of about 7 and 9% respectively, in good agreement with the frequency of presenting individuals in the panel of healthy donors analyzed.

TABLE II

The ability of APC bearing different HLA-DP alleles to present peptide SSX-2 13-34 (SEQ ID NO: 1) was assessed by intracellular IFN-γ secretion

| APC | HLA-DP | SSX-2$_{13-34}$ (SEQ ID NO: 1) presentation |
|---|---|---|
| LAU 672/DC | 101-402 | + |
| LAU 149/EBV | 301-401 | + |
| LAU 465/DC | 101-401 | + |
| LAU 42/EBV | 401-501 | − |
| LAU 50/TCL | 401-402 | − |

Example 4

Figure 4A:
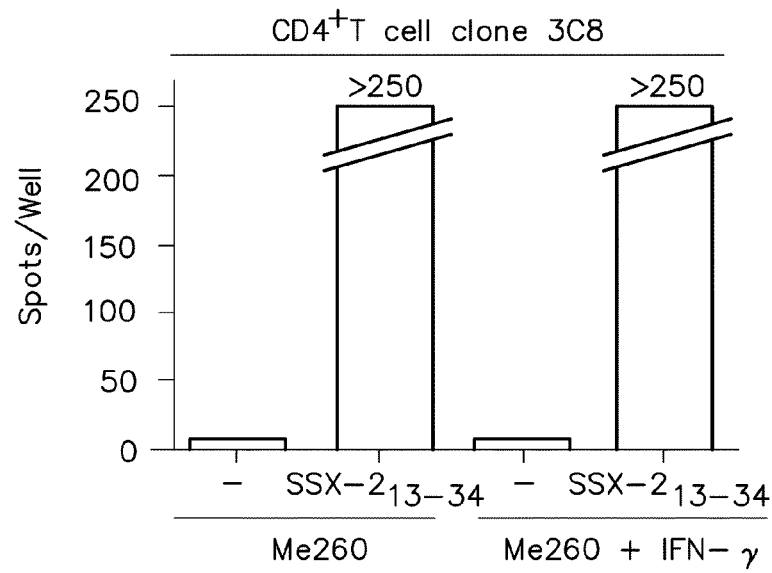
FIGS. 4A and 4B show the lack of tumor recognition by SSX-2 13-34 specific CD4+ T cells.
Figure 4B:
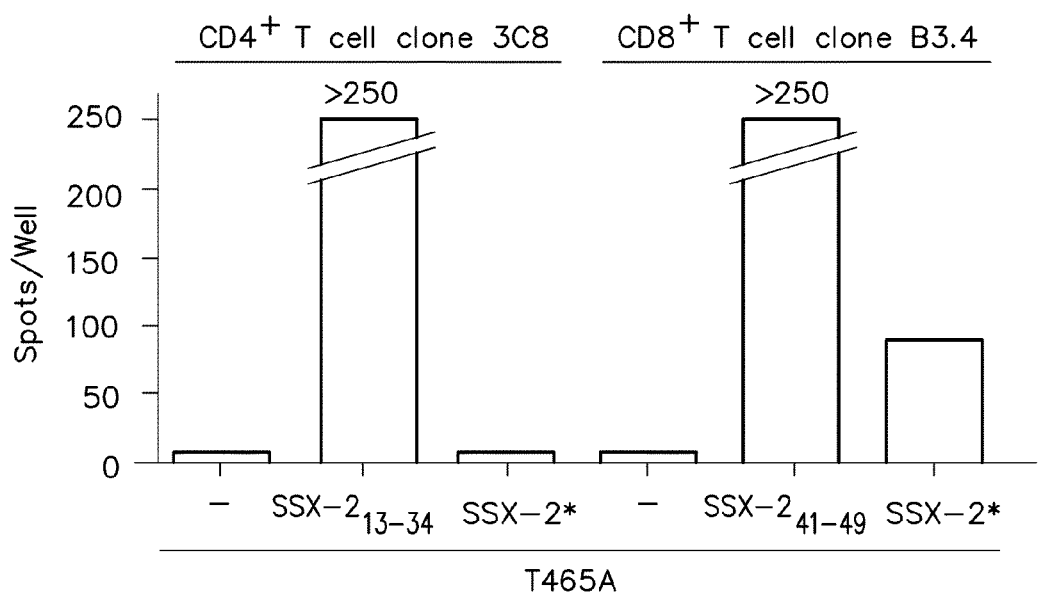

The T Cell Epitope Recognized by SSX-2 Specific CD4+ T Cells from LAU 672 is not Presented by Tumor Cells but is Efficiently Processed and Presented by Professional Antigen Presenting Cells To assess if the T cell epitope recognized by SSX-2 specific CD4+ T cells from LAU 672 is naturally presented on the surface of tumor cells, we tested different melanoma cells lines for their capacity to present peptide SSX-2 13-34 (SEQ ID NO:1) to specific T cell clones. We identified two lines that efficiently presented the peptide indicating expression of the appropriate restriction elements (FIG. 4). One of these lines (Me 260, derived from to patient LAU 149) expressed SSX-2, but was not recognized by CD4+ T cells in the absence of exogenously added peptide. Because the expression level of HLA-DP in this line was low, we treated the cells with IFN-γ for 48 hr. This resulted in increased expression of HLA-DP (not shown) but not in recognition of endogenously expressed antigen (FIG. 4). The second melanoma cell line (T465A derived from patient LAU465) able to present peptide SSX-2 13-34 to specific CD4+ T cells was SSX-2 negative but expressed HLA-A2 and relatively high levels of HLA-DP (not shown). Transfection of T465A cells with SSX-2 did not result in recognition by specific CD4+ T cells. In contrast T465A cells transfected with a plasmid encoding SSX-2 were recognized by CD8+ T cells specific for peptide SSX-2 41-49 (FIG. 4). Similar results were obtained upon IFN-γ treatment. Together these results indicate that the T cell epitope recognized by SSX-2 specific CD4+ T cells from LAU 672 is not presented by tumor cells at levels sufficient to allow direct recognition of SSX-2 expressing tumors.

Figure 5A:
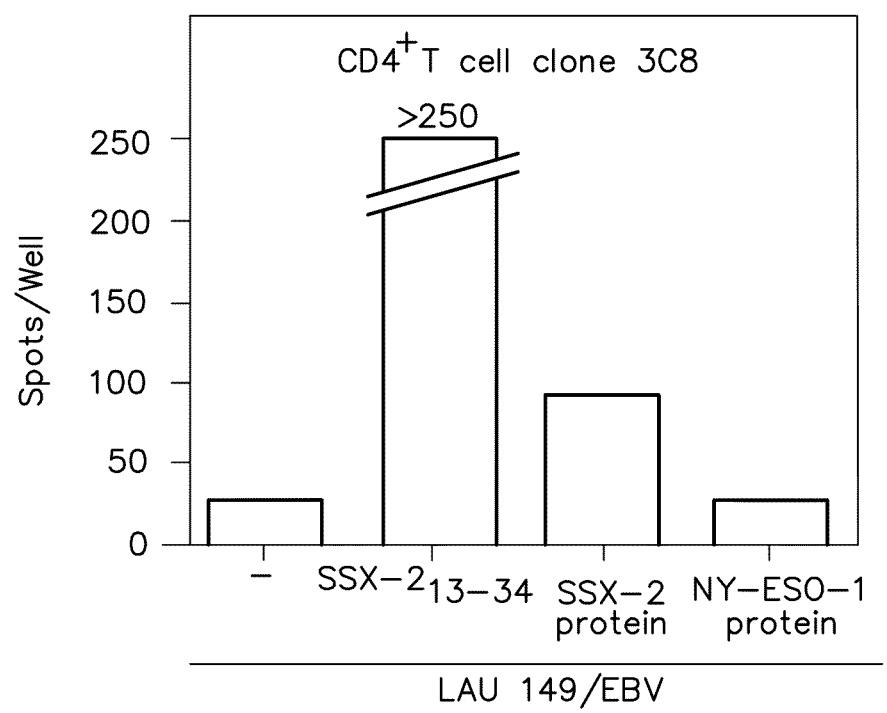
FIGS. 5A-5C show that the SSX-2 epitope recognized by 13-34 specific CD4+ T cells is efficiently processed and presented by professional APC.
Figure 5B:
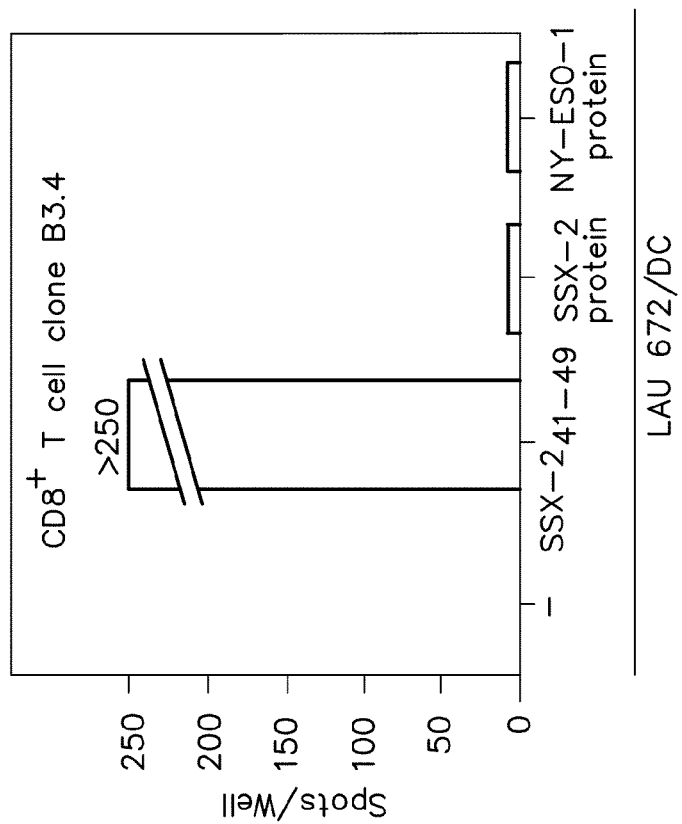
Figure 5C:
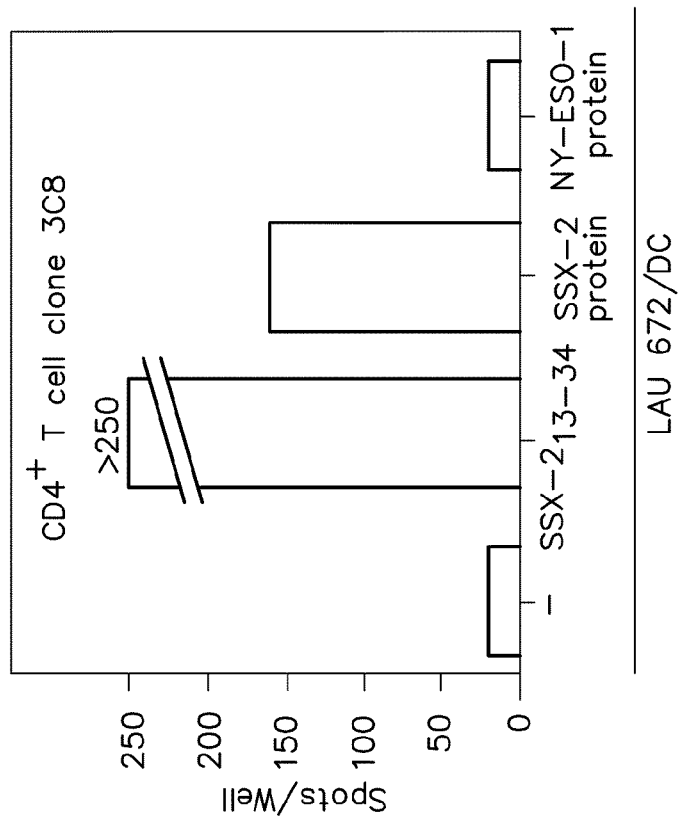

We then assessed the ability of professional APC to process the SSX-2 antigen and present the SSX-2 13-34 epitope to specific CD4+ T cells. As illustrated in FIG. 5A, EBV cells from patient LAU 149 (EBV LAU 149) were able to efficiently process the SSX-2 protein and present the relevant epitope to the SSX-2 13-34 specific CD4+ T cell clone 3C8. The clone was not significantly stimulated by incubation with the SSX-2 protein in the presence of EBV cells unable to present the peptide or by incubation of EBV LAU 149 with NY-ESO-1 protein. Efficient presentation was also obtained by using LAU 672 autologous dendritic cells (DC) (FIG. 5B). Interestingly, both in the case of EBV and DC, processing of exogenous SSX-2 protein did not result in recognition of the CD8+ T cell epitope SSX-2 41-49 by specific clonal CD8+ T cells (clone B3.4, FIG. 5B).

In this study, we have used a mixture composed of 20-22 amino acid long peptides spanning the SSX-2 protein sequence and overlapping by 10 amino acids, to stimulate enriched CD4+ T lymphocytes from an SSX-2 expressing melanoma patient with autologous irradiated CD4− cells. After a single in vitro stimulation, peptide submixtures, and then single peptides, were used for screening together with autologous PBMC as a source of APC. This simple procedure allowed the identification of the first SSX-2 derived CD4+ T cell epitope. Once the reactive peptide in the active mixture was identified, specific CD4+ T cells were isolated using a cytokine secretion based cell sorting procedure and cloned by mitogen to stimulation under limiting dilution conditions. All clonal populations isolated were specific. Specific clonal populations were then used to further characterize the identified epitope.

After a single stimulation, about 1% of CD4+ T cells in the culture specifically secreted IFN-γ in response to antigen stimulation, suggesting that a relatively high frequency of these cells may be present in circulating lymphocytes from melanoma patient LAU 672, most likely as the result of a spontaneous response to the patient's autologous SSX-2 expressing tumor. In support of this, no response to the identified epitope was detected, by using the same methodology, in normal donors expressing the appropriate MHC Class II restriction element. It is noteworthy that we have previously found a spontaneous response to the CD8+ T cell epitope 41-49 in both circulating and tumor infiltrating lymphocytes of patient LAU 672. We failed to detect SSX-2 13-34 specific cells among unstimulated CD4+ T cells from the patient by using ELISPOT, indicating that, although remarkably elevated after a single cycle of in vitro stimulation, the frequency of these cells was below ELISPOT detection limits ex vivo. No specific responses to the SSX-2 spanning peptides mix were detected using the same method in the case of four additional melanoma patients bearing SSX-2 expressing tumors including one (LAU 149) whose APC were able to present the SSX-2 13-34 epitope to specific CD4+ T cells. This suggests that spontaneous CD4+ T cell responses to SSX-2 could be relatively rare, even among patients bearing antigen expressing tumors.

It is noteworthy that a high degree of homology exists between SSX-2 and other SSX family members. In particular, the sequence of the SSX-2 CD4$^+$ T cell epitope identified here is identical to that of SSX-3 whereas in the case of other SSX family members (e.g., SSX-1, SSX-4 and SSX-5; see Gure et al., Int. J. Cancer 101 (5), 448-453, 2002) differences of several amino acids are present in this region of the corresponding proteins. For some of the shorter peptides demonstrated herein as having HLA class II binding activity and other activities, several of the peptides encoded by other SSX genes are very similar or identical. These related peptides (see Table III; including equivalent fragments as shown elsewhere herein for SSX-2) are believed to be functional variants of the SSX-2 peptides presented herein, except for SSX-5 isoform a (SEQ ID NO:43), which varies significantly in amino acid sequence. The analysis of CD8$^+$ and CD4$^+$ T cell response to other SSX proteins, especially SSX-1 and SSX-4, that are, together with SSX-2, the most frequently expressed in tumors, is relevant to the development of generic cancer vaccine.

TABLE III

Related SSX family peptides (amino acid 13-34 regions)

| Gene/Location | Accession No. | Amino Acid Sequence | SEQ ID NO |
|---|---|---|---|
| SSX-2$_{13-34}$ | NM_003147 (isoform a); NM_175698 (isoform b) | VGAQIPEKIQKAFDDIAKYFSK | 1 |
| SSX-2$_{19-30}$ | | EKIQKAFDDIAK | 8 |
| SSX-1$_{13-34}$ | NM_005635 | DDAKASEKRSKAFDDIAT**YFSK | 40 |
| SSX-3$_{13-34}$ | NM_021014 (isoform a); NM_175711 (isoform b) | VGAQIPEKIQKAFDDIAKYFSK | 41 |
| SSX-4$_{13-34}$ | NM_005636 (isoform a); NM_175729 (isoform b) | DDAQISEKLRKAFDDIAKYFSK | 42 |
| SSX-5$_{13-34}$ | NM_021015 (isoform a) | VGSQIPEKMQKHPWRQVCDRGI | 43 |
| SSX-5$_{13-34}$ | NM_175723 (isoform b) | VGSQIPEKMQKAFDDIAKYFSE | 44 |
| SSX-6$_{13-34}$ | NM_173357 | DDAKASEKRSKAFDDIAKYFSK | 45 |
| SSX-7$_{13-34}$ | NM_173358 | AGAQIPEKIQKSFDDIAKYFSK | 46 |
| SSX-8$_{13-34}$ | BK000688 | DDDKASEKRSKAFNDIATYFSK | 47 |
| SSX-9$_{13-34}$ | BK000689 | AGSQIPEKIQKAFDDIAKYFSK | 48 |

Area corresponding to SEQ ID NO: 8 is underlined; amino acid differences in this area of SSX peptides relative to SEQ ID NO: 8 are in bold.

The recognition of the identified SSX-2 epitope by specific CD4+ T cells was HLA-DP restricted. In support of the importance of DP-restricted immune responses, including those against tumors, two tumor antigen derived epitopes (from MAGE-A3 and NY-ESO-1) recognized by CD4+ T cells in association with the HLA-DP4 molecule have been recently identified (Zeng et al., Proc Natl Acad Sci USA 98:3964-3969, 2001; Schultz et al., Cancer Res 60:6272-6275, 2000). Recognition of SSX-2 13-34 by CD4+ T cells from patient LAU 672 was restricted by at least two other HLA-DP molecules. These molecules, HLA-DP101 and DP301 are, after DP4, the most prevalent DP alleles. Interestingly, they are characterized together with DP9 by the presence of D at position β86 and may possibly define a separate supertype of peptide binding specificity.

SSX-2 13-34 specific CD4$^+$ T cells from patient LAU 672 failed to recognize SSX-2+ tumor cells expressing the presenting restriction allele, indicating that the identified epitope was not expressed at levels sufficient to allow direct recognition of tumor cells even in the case they express MHC Class II. However, both EBV cells and, even more efficiently, DC were able to process the native antigen (given to APC in the form of recombinant SSX-2 protein) and present the relevant epitope to specific CD4$^+$ T cells. MHC-class II restricted recognition of antigens (including tumor antigens) can follow different presentation pathways. Exogenous proteins captured by the APC by endocytosis reach the endocytic pathway and, are cleaved by proteases into peptides that then associate to MHC Class II molecules. Endogenously produced proteins such as secretory or membrane-associated can also follow the exogenous class II presentation pathway, whereas other endogenous proteins such as melanosomal proteins contain sequences that directly target them to endosomes. In addition there is growing evidence that other self-proteins not containing endosomal targeting sequences can also gain access to the endogenous class II presentation pathway. The epitope target of the spontaneous CD4$^+$ T cell response in patient LAU 672 required processing and presentation of antigen by autologous DC for CD4$^+$ T cell activation to occur. Thus, it is likely that processing and presentation of tumor-derived SSX-2 antigen by autologous professional APC through the exogenous pathway was the mechanism through which this spontaneous CD4$^+$ T cell response to the autologous tumors occurred in vivo. CD4$^+$ T cells that recognize tumor antigen epitopes expressed by tumor cells have also been previously isolated from healthy donors or cancer patients (Zeng et al., 2001; Manici et al., J Exp Med 189:871-876, 1999). Interestingly, in the case of the MAGE-A3 antigen both CD4+ T cell epitopes that are presented or not by antigen expressing tumors have been described (Chaux et al., J Exp Med 189: 767-778, 1999; Schultz et al., 2000; Manici et al., 1999). Thus the identification of an SSX-2 derived CD4$^+$ T cell epitope that is not expressed by tumor cells does not necessarily imply that this nuclear antigen does not have access to the endogeneous class-II presentation pathway.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule encoding an SSX-2 HLA class II-binding peptide comprising an endosomal targeting signal, wherein the SSX2 HLA class II-binding peptide consists of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

2. The isolated nucleic acid molecule of claim 1, wherein the HLA-class II binding peptide consists of an amino acid sequence selected from the group consisting of SEQ ID NO:1, SEQ ID NO:2, SEQ ID NO:3, SEQ ID NO:4, SEQ ID NO:5, SEQ ID NO:6 and SEQ ID NO:7.

3. The isolated nucleic acid molecule of claim 2, wherein the HLA-class II binding peptide consists of an amino acid sequence selected from the group consisting of SEQ ID NO:1, SEQ ID NO:5, and SEQ ID NO:6.

4. The isolated nucleic acid molecule of claim 3, wherein the HLA-class II binding peptide consists of the amino acid sequence set forth as SEQ ID NO:1.

5. The isolated nucleic acid molecule of claim 1, wherein the endosomal targeting signal comprises an endosomal targeting portion of human invariant chain Ii.

6. A composition comprising an isolated nucleic acid molecule encoding an SSX-2 HLA class I-binding peptide and an isolated nucleic acid molecule encoding an SSX-2 HLA class II-binding peptide comprising an endosomal targeting signal, wherein the isolated SSX-2 HLA class II-binding peptide consists of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

7. The composition of claim 6, wherein the endosomal targeting signal comprises an endosomal targeting portion of human invariant chain Ii.

8. A composition comprising one or more of the isolated nucleic acid molecules encoding an SSX-2 HLA class II-binding peptides of claim 1 and an isolated nucleic acid molecule encoding one or more HLA class II molecules.

* * * * *

SEQUENCE LISTING

<160> NUMBER OF SEQ ID NOS: 48

<210> SEQ ID NO 1
<211> LENGTH: 22
<212> TYPE: PRT
<213> ORGANISM: Homo sapiens

<400> SEQUENCE: 1

Val Gly Ala Gln Ile Pro Glu Lys Ile Gln Lys Ala Phe Asp Asp Ile
1               5                   10                  15

Ala Lys Tyr Phe Ser Lys
            20

<210> SEQ ID NO 2
<211> LENGTH: 24
<212> TYPE: PRT
<213> ORGANISM: Homo sapiens

<400> SEQUENCE: 2

Val Gly Ala Gln Ile Pro Glu Lys Ile Gln Lys Ala Phe Asp Asp Ile
1               5                   10                  15

Ala Lys Tyr Phe Ser Lys Glu Glu
            20

<210> SEQ ID NO 3
<211> LENGTH: 20
<212> TYPE: PRT
<213> ORGANISM: Homo sapiens

<400> SEQUENCE: 3

Val Gly Ala Gln Ile Pro Glu Lys Ile Gln Lys Ala Phe Asp Asp Ile
1               5                   10                  15

Ala Lys Tyr Phe
            20

<210> SEQ ID NO 4
<211> LENGTH: 18
<212> TYPE: PRT
<213> ORGANISM: Homo sapiens

<400> SEQUENCE: 4

Val Gly Ala Gln Ile Pro Glu Lys Ile Gln Lys Ala Phe Asp Asp Ile
1               5                   10                  15

Ala Lys

<210> SEQ ID NO 5
<211> LENGTH: 18
<212> TYPE: PRT
<213> ORGANISM: Homo sapiens

<400> SEQUENCE: 5

Ile Pro Glu Lys Ile Gln Lys Ala Phe Asp Asp Ile Ala Lys Tyr Phe
1               5                   10                  15

Ser Lys

<210> SEQ ID NO 6
<211> LENGTH: 16
<212> TYPE: PRT
<213> ORGANISM: Homo sapiens

```
<400> SEQUENCE: 6

Glu Lys Ile Gln Lys Ala Phe Asp Asp Ile Ala Lys Tyr Phe Ser Lys
1               5                   10                  15

<210> SEQ ID NO 7
<211> LENGTH: 14
<212> TYPE: PRT
<213> ORGANISM: Homo sapiens

<400> SEQUENCE: 7

Ile Gln Lys Ala Phe Asp Asp Ile Ala Lys Tyr Phe Ser Lys
1               5                   10

<210> SEQ ID NO 8
<211> LENGTH: 12
<212> TYPE: PRT
<213> ORGANISM: Homo sapiens

<400> SEQUENCE: 8

Glu Lys Ile Gln Lys Ala Phe Asp Asp Ile Ala Lys
1               5                   10

<210> SEQ ID NO 9
<211> LENGTH: 1322
<212> TYPE: DNA
<213> ORGANISM: Homo sapiens
<220> FEATURE:
<221> NAME/KEY: CDS
<222> LOCATION: (109)..(675)

<400> SEQUENCE: 9
gcatgctctg actttctctc tctttcgatt cttccatact cagagtacgc acggtctgat      60
tttctctttg gattcttcca aaatcagagt cagactgctc ccggtgcc atg aac gga     117
                                                    Met Asn Gly
                                                    1 gac gac gcc ttt gca agg aga ccc acg gtt ggt gct caa ata cca gag     165
Asp Asp Ala Phe Ala Arg Arg Pro Thr Val Gly Ala Gln Ile Pro Glu
        5                   10                  15 aag atc caa aag gcc ttc gat gat att gcc aaa tac ttc tct aag gaa     213
Lys Ile Gln Lys Ala Phe Asp Asp Ile Ala Lys Tyr Phe Ser Lys Glu
20                  25                  30                  35 gag tgg gaa aag atg aaa gcc tcg gag aaa atc ttc tat gtg tat atg     261
Glu Trp Glu Lys Met Lys Ala Ser Glu Lys Ile Phe Tyr Val Tyr Met
            40                  45                  50 aag aga aag tat gag gct atg act aaa cta ggt ttc aag gcc acc ctc     309
Lys Arg Lys Tyr Glu Ala Met Thr Lys Leu Gly Phe Lys Ala Thr Leu
        55                  60                  65 cca cct ttc atg tgt aat aaa cgg gcc gaa gac ttc cag ggg aat gat     357
Pro Pro Phe Met Cys Asn Lys Arg Ala Glu Asp Phe Gln Gly Asn Asp
    70                  75                  80 ttg gat aat gac cct aac cgt ggg aat cag gtt gaa cgt cct cag atg     405
Leu Asp Asn Asp Pro Asn Arg Gly Asn Gln Val Glu Arg Pro Gln Met
85                  90                  95 act ttc ggc agg ctc cag gga atc tcc ccg aag atc atg ccc aag aag     453
Thr Phe Gly Arg Leu Gln Gly Ile Ser Pro Lys Ile Met Pro Lys Lys
100                 105                 110                 115 cca gca gag gaa gga aat gat tcg gag gaa gtg cca gaa gca tct ggc     501
Pro Ala Glu Glu Gly Asn Asp Ser Glu Glu Val Pro Glu Ala Ser Gly
            120                 125                 130 cca caa aat gat ggg aaa gag ctg tgc ccc ccg gga aaa cca act acc     549
Pro Gln Asn Asp Gly Lys Glu Leu Cys Pro Pro Gly Lys Pro Thr Thr
        135                 140                 145
```

```
tct gag aag att cac gag aga tct gga ccc aaa agg ggg gaa cat gcc      597
Ser Glu Lys Ile His Glu Arg Ser Gly Pro Lys Arg Gly Glu His Ala
        150                 155                 160 tgg acc cac aga ctg cgt gag aga aaa cag ctg gtg att tat gaa gag      645
Trp Thr His Arg Leu Arg Glu Arg Lys Gln Leu Val Ile Tyr Glu Glu
165                 170                 175 atc agc gac cct gag gaa gat gac gag taa ctcccctcag ggatacgaca        695
Ile Ser Asp Pro Glu Glu Asp Asp Glu
180                 185 catgcccatg atgagaagca gaacgtggtg acctttcacg aacatgggca tggctgcgga    755
cccctcgtca tcaggtgcat agcaagtgaa agcaagtgtt cacaacagtg aaaagttgag    815
cgtcattttt cttagtgtgc caagagttcg atgttagcgt ttacgttgta ttttcttaca    875
ctgtgtcatt ctgttagata ctaacatttt cattgatgag caagacatac ttaatgcata    935
ttttggtttg tgtatccatg cacctacctt agaaaacaag tattgtcggt tacctctgca    995
tggaacagca ttaccctcct ctctccccag atgtgactac tgagggcagt tctgagtgtt   1055
taatttcaga ttttttcctc tgcatttaca cacacacgca cacaaaccac accacacaca   1115
cacacacaca cacacacaca cacacacaca cacaccaagt accagtataa gcatctgcca   1175
tctgcttttc ccattgccat gcgtcctggt caagctcccc tcactctgtt tcctggtcag   1235
catgtactcc cctcatccga ttcccctgta gcagtcactg acagttaata aacctttgca   1295
aacgttcaaa aaaaaaaaaa aaaaaaa                                       1322

<210> SEQ ID NO 10
<211> LENGTH: 188
<212> TYPE: PRT
<213> ORGANISM: Homo sapiens

<400> SEQUENCE: 10

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185
```

```
<210> SEQ ID NO 11
<211> LENGTH: 1466
<212> TYPE: DNA
<213> ORGANISM: Homo sapiens
<220> FEATURE:
<221> NAME/KEY: CDS
<222> LOCATION: (109)..(780)

<400> SEQUENCE: 11
gcatgctctg actttctctc tctttcgatt cttccatact cagagtacgc acggtctgat        60
tttctctttg gattcttcca aaatcagagt cagactgctc ccggtgcc atg aac gga       117
                                                    Met Asn Gly
                                                      1 gac gac gcc ttt gca agg aga ccc acg gtt ggt gct caa ata cca gag        165
Asp Asp Ala Phe Ala Arg Arg Pro Thr Val Gly Ala Gln Ile Pro Glu
      5                  10                  15 aag atc caa aag gcc ttc gat gat att gcc aaa tac ttc tct aag gaa        213
Lys Ile Gln Lys Ala Phe Asp Asp Ile Ala Lys Tyr Phe Ser Lys Glu
 20                  25                  30                  35 gag tgg gaa aag atg aaa gcc tcg gag aaa atc ttc tat gtg tat atg        261
Glu Trp Glu Lys Met Lys Ala Ser Glu Lys Ile Phe Tyr Val Tyr Met
                 40                  45                  50 aag aga aag tat gag gct atg act aaa cta ggt ttc aag gcc acc ctc        309
Lys Arg Lys Tyr Glu Ala Met Thr Lys Leu Gly Phe Lys Ala Thr Leu
             55                  60                  65 cca cct ttc atg tgt aat aaa cgg gcc gaa gac ttc cag ggg aat gat        357
Pro Pro Phe Met Cys Asn Lys Arg Ala Glu Asp Phe Gln Gly Asn Asp
         70                  75                  80 ttg gat aat gac cct aac cgt ggg aat cag gtt gaa cgt cct cag atg        405
Leu Asp Asn Asp Pro Asn Arg Gly Asn Gln Val Glu Arg Pro Gln Met
 85                  90                  95 act ttc ggc agg ctc cag gga atc tcc ccg aag atc atg ccc aag aag        453
Thr Phe Gly Arg Leu Gln Gly Ile Ser Pro Lys Ile Met Pro Lys Lys
100                 105                 110                 115 cca gca gag gaa gga aat gat tcg gag gaa gtg cca gaa gca tct ggc        501
Pro Ala Glu Glu Gly Asn Asp Ser Glu Glu Val Pro Glu Ala Ser Gly
                120                 125                 130 cca caa aat gat ggg aaa gag ctg tgc ccc ccg gga aaa cca act acc        549
Pro Gln Asn Asp Gly Lys Glu Leu Cys Pro Pro Gly Lys Pro Thr Thr
            135                 140                 145 tct gag aag att cac gag aga tct gga aat agg gag gcc caa gaa aag        597
Ser Glu Lys Ile His Glu Arg Ser Gly Asn Arg Glu Ala Gln Glu Lys
        150                 155                 160 gaa gag aga cgc gga aca gct cat cgg tgg agc agt cag aac aca cac        645
Glu Glu Arg Arg Gly Thr Ala His Arg Trp Ser Ser Gln Asn Thr His
    165                 170                 175 aac att ggt cga ttc agt ttg tca act tct atg ggt gca gtt cat ggt        693
Asn Ile Gly Arg Phe Ser Leu Ser Thr Ser Met Gly Ala Val His Gly
180                 185                 190                 195 acc ccc aaa aca att aca cac aac agg gac cca aaa ggg ggg aac atg        741
Thr Pro Lys Thr Ile Thr His Asn Arg Asp Pro Lys Gly Gly Asn Met
                200                 205                 210 cct gga ccc aca gac tgc gtg aga gaa aac agc tgg tga tttatgaaga        790
Pro Gly Pro Thr Asp Cys Val Arg Glu Asn Ser Trp
            215                 220 gatcagcgac cctgaggaag atgacgagta actcccctca gggatacgac acatgcccat      850
gatgagaagc agaacgtggt gacctttcac gaacatgggc atggctgcgg accccctcgtc     910 atcaggtgca tagcaagtga aagcaagtgt tcacaacagt gaaagttga gcgtcatttt       970 tcttagtgtg ccaagagttc gatgttagcg tttacgttgt attttcttac actgtgtcat     1030
```

```
tctgttagat actaacattt tcattgatga gcaagacata cttaatgcat attttggttt    1090
gtgtatccat gcacctacct tagaaaacaa gtattgtcgg ttacctctgc atggaacagc    1150
attaccctcc tctctcccca gatgtgacta ctgagggcag ttctgagtgt ttaatttcag    1210
attttttcct ctgcatttac acacacacgc acacaaacca caccacacac acacacacac    1270
acacacacac acacacacac acacaccaag taccagtata agcatctgcc atctgctttt    1330
cccattgcca tgcgtcctgg tcaagctccc ctcactctgt ttcctggtca gcatgtactc    1390
ccctcatccg attcccctgt agcagtcact gacagttaat aaacctttgc aaacgttcaa    1450
aaaaaaaaaa aaaaa                                                    1466

<210> SEQ ID NO 12
<211> LENGTH: 223
<212> TYPE: PRT
<213> ORGANISM: Homo sapiens

<400> SEQUENCE: 12

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Asn Arg Glu Ala
145                 150                 155                 160

Gln Glu Lys Glu Glu Arg Arg Gly Thr Ala His Arg Trp Ser Ser Gln
                165                 170                 175

Asn Thr His Asn Ile Gly Arg Phe Ser Leu Ser Thr Ser Met Gly Ala
            180                 185                 190

Val His Gly Thr Pro Lys Thr Ile Thr His Asn Arg Asp Pro Lys Gly
        195                 200                 205

Gly Asn Met Pro Gly Pro Thr Asp Cys Val Arg Glu Asn Ser Trp
    210                 215                 220

<210> SEQ ID NO 13
<211> LENGTH: 1274
<212> TYPE: DNA
<213> ORGANISM: Homo sapiens
<220> FEATURE:
<221> NAME/KEY: CDS
<222> LOCATION: (94)..(603)
<220> FEATURE:
<221> NAME/KEY: misc_feature
<222> LOCATION: (547)..(560)
<223> OTHER INFORMATION: n is a, c, g, or t
```

<400> SEQUENCE: 13

```
ctctctcttt cgattcttcc atactcagag tacgcacggt ctgattttct ctttggattc      60
ttccaaaatc agagtcagac tgctcccggt gcc atg aac gga gac gac gcc ttt     114
                                  Met Asn Gly Asp Asp Ala Phe
                                  1               5 gca agg aga ccc acg gtt ggt gct caa ata cca gag aag atc caa aag     162
Ala Arg Arg Pro Thr Val Gly Ala Gln Ile Pro Glu Lys Ile Gln Lys
     10                  15                  20 gcc ttc gat gat att gcc aaa tac ttc tct aag gaa gag tgg gaa aag     210
Ala Phe Asp Asp Ile Ala Lys Tyr Phe Ser Lys Glu Glu Trp Glu Lys
 25                  30                  35 atg aaa gcc tcg gag aaa atc ttc tat gtg tat atg aag aga aag tat     258
Met Lys Ala Ser Glu Lys Ile Phe Tyr Val Tyr Met Lys Arg Lys Tyr
40                  45                  50                  55 gag gct atg act aaa cta ggt ttc aag gcc acc ctc cca cct ttc atg     306
Glu Ala Met Thr Lys Leu Gly Phe Lys Ala Thr Leu Pro Pro Phe Met
                 60                  65                  70 tgt aat aaa cgg gcc gaa gac ttc cag ggg aat gat ttg gat aat gac     354
Cys Asn Lys Arg Ala Glu Asp Phe Gln Gly Asn Asp Leu Asp Asn Asp
             75                  80                  85 cct aac cgt ggg aat cag gtt gaa cgt cct cag atg act ttc ggc agg     402
Pro Asn Arg Gly Asn Gln Val Glu Arg Pro Gln Met Thr Phe Gly Arg
         90                  95                 100 ctc cag gga atc tcc ccg aag atc atg ccc aag aag cca gca gag gaa     450
Leu Gln Gly Ile Ser Pro Lys Ile Met Pro Lys Lys Pro Ala Glu Glu
     105                 110                 115 gga aat gat tcg gag gaa gtg cca gaa gca tct ggc cca caa aat gat     498
Gly Asn Asp Ser Glu Glu Val Pro Glu Ala Ser Gly Pro Gln Asn Asp
120                 125                 130                 135 ggg aaa gag ctg tgc ccc ccg gga aaa cca act acc tct gag aag att     546
Gly Lys Glu Leu Cys Pro Pro Gly Lys Pro Thr Thr Ser Glu Lys Ile
                 140                 145                 150 nnn nnn nnn nnn nng acc caa aag ggg gga aca tgc ctg gac cca cag     594
Xaa Xaa Xaa Xaa Xaa Thr Gln Lys Gly Gly Thr Cys Leu Asp Pro Gln
             155                 160                 165 act gcg tga gagaaaacag ctggtgattt atgaagagat cagcgaccct              643
Thr Ala gaggaagatg acgagtaact cccctcgggg atacgacaca tgcccatgat gagaagtaga     703
acgtggtgac ctttcacgaa cataggcatg gctgcggacc cctcgtcatc aggtgcatag     763
caagtgaaag caagtgttca caacagtgaa aagttgagcg tcgttttct tagtgtgaca      823 agagttcgat gttagtgttt ccattgtatt tcttacagt gtgccattct gttagatatt      883
agcgttttca ttgatgagca agacatgctt aatgtgtatt tcggtttgtg tatccatgca     943
cctacctcag aaagcaagta tagtcaggta ttctctccat agaacagcac taccctcctc    1003
tctccccaga tgtgactact gagggcagat ctgagtgttt aatttccgat tttcccctct    1063
gcatttacac accagacaca caaacacaca cacacagaca cacacacaca cagacacacc    1123
aagtaccagt ataagcatct cccatatgct tttccccatt gccatgagtc ctggtcaagc    1183 ccccccttcaa tttgttttcct gttcagcatg tactccctcc tctgattcc ccgtatcagt    1243 cactgacagt taatacacct ttgcaaacgt t                                    1274
```

<210> SEQ ID NO 14
<211> LENGTH: 169
<212> TYPE: PRT
<213> ORGANISM: Homo sapiens

```
<220> FEATURE:
<221> NAME/KEY: misc_feature
<222> LOCATION: (152)..(152)
<223> OTHER INFORMATION: The 'Xaa' at location 152 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (153)..(153)
<223> OTHER INFORMATION: The 'Xaa' at location 153 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (154)..(154)
<223> OTHER INFORMATION: The 'Xaa' at location 154 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (155)..(155)
<223> OTHER INFORMATION: The 'Xaa' at location 155 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (156)..(156)
<223> OTHER INFORMATION: The 'Xaa' at location 156 stands for Lys, Arg,
      Thr, Met, Glu, Gly, Ala, Val, Gln, Pro, Leu, Trp, or Ser.

<400> SEQUENCE: 14

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile Xaa Xaa Xaa Xaa Xaa Thr Gln Lys Gly
145                 150                 155                 160

Gly Thr Cys Leu Asp Pro Gln Thr Ala
                165

<210> SEQ ID NO 15
<211> LENGTH: 66
<212> TYPE: DNA
<213> ORGANISM: Homo sapiens
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
```

<400> SEQUENCE: 15
gttggggccc aaattcccga aaaaatccaa aaagcntttg atgatattgc naaatatttt    60
agtaaa                                                               66

<210> SEQ ID NO 16
<211> LENGTH: 72
<212> TYPE: DNA
<213> ORGANISM: Homo sapiens
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 16
gttggggccc aaattcccga aaaaatccaa aaagcntttg atgatattgc naaatatttt    60
agtaaagaag aa                                                        72

<210> SEQ ID NO 17
<211> LENGTH: 60
<212> TYPE: DNA
<213> ORGANISM: Homo sapiens
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 17
gttggggccc aaattcccga aaaaatccaa aaagcntttg atgatattgc naaatatttt    60

<210> SEQ ID NO 18
<211> LENGTH: 54
<212> TYPE: DNA
<213> ORGANISM: Homo sapiens
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 18
gttggggccc aaattcccga aaaaatccaa aaagcntttg atgatattgc naaa          54

<210> SEQ ID NO 19
<211> LENGTH: 54
<212> TYPE: DNA
<213> ORGANISM: Homo sapiens
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 19
attcccgaaa aaatccaaaa agcntttgat gatattgcna aatattttag taaa           54

```
<210> SEQ ID NO 20
<211> LENGTH: 48
<212> TYPE: DNA
<213> ORGANISM: Homo sapiens
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 20
gaaaaaatcc aaaaagcntt tgatgatatt gcnaaatatt ttagtaaa            48

<210> SEQ ID NO 21
<211> LENGTH: 48
<212> TYPE: DNA
<213> ORGANISM: Homo sapiens
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 21
gaaaaaatcc aaaaagcntt tgatgatatt gcnaaatatt ttagtaaa            48

<210> SEQ ID NO 22
<211> LENGTH: 22
<212> TYPE: DNA
<213> ORGANISM: Homo sapiens

<400> SEQUENCE: 22
atgcgccctg aagacagaat gt                                       22

<210> SEQ ID NO 23
<211> LENGTH: 26
<212> TYPE: DNA
<213> ORGANISM: Homo sapiens

<400> SEQUENCE: 23
tcacagggtc ccctgggccc ggggga                                   26

<210> SEQ ID NO 24
<211> LENGTH: 22
<212> TYPE: DNA
<213> ORGANISM: Homo sapiens

<400> SEQUENCE: 24
atgatggttc tgcaggtttc tg                                       22

<210> SEQ ID NO 25
<211> LENGTH: 25
<212> TYPE: DNA
<213> ORGANISM: Homo sapiens

<400> SEQUENCE: 25
ttatgcagat cctcgttgaa ctttc                                    25
```

```
<210> SEQ ID NO 26
<211> LENGTH: 22
<212> TYPE: PRT
<213> ORGANISM: Homo sapiens

<400> SEQUENCE: 26

Met Asn Gly Asp Asp Ala Phe Ala Arg Arg Pro Thr Val Gly Ala Gln
1               5                   10                  15

Ile Pro Glu Lys Ile Gln
            20

<210> SEQ ID NO 27
<211> LENGTH: 22
<212> TYPE: PRT
<213> ORGANISM: Homo sapiens

<400> SEQUENCE: 27

Phe Asp Asp Ile Ala Lys Tyr Phe Ser Lys Glu Glu Trp Glu Lys Met
1               5                   10                  15

Lys Ala Ser Glu Lys Ile
            20

<210> SEQ ID NO 28
<211> LENGTH: 22
<212> TYPE: PRT
<213> ORGANISM: Homo sapiens

<400> SEQUENCE: 28

Trp Glu Lys Met Lys Ala Ser Glu Lys Ile Phe Tyr Val Tyr Met Lys
1               5                   10                  15

Arg Lys Tyr Glu Ala Met
            20

<210> SEQ ID NO 29
<211> LENGTH: 22
<212> TYPE: PRT
<213> ORGANISM: Homo sapiens

<400> SEQUENCE: 29

Val Tyr Met Lys Arg Lys Tyr Glu Ala Met Thr Lys Leu Gly Phe Lys
1               5                   10                  15

Ala Thr Leu Pro Pro Phe
            20

<210> SEQ ID NO 30
<211> LENGTH: 22
<212> TYPE: PRT
<213> ORGANISM: Homo sapiens

<400> SEQUENCE: 30

Leu Gly Phe Lys Ala Thr Leu Pro Pro Phe Met Cys Asn Lys Arg Ala
1               5                   10                  15

Glu Asp Phe Gln Gly Asn
            20

<210> SEQ ID NO 31
<211> LENGTH: 22
<212> TYPE: PRT
<213> ORGANISM: Homo sapiens
```

```
<400> SEQUENCE: 31

Asn Lys Arg Ala Glu Asp Phe Gln Gly Asn Asp Leu Asp Asn Asp Pro
1               5                   10                  15

Asn Arg Gly Asn Gln Val
            20

<210> SEQ ID NO 32
<211> LENGTH: 19
<212> TYPE: PRT
<213> ORGANISM: Homo sapiens

<400> SEQUENCE: 32

Asp Pro Asn Arg Gly Asn Gln Val Glu Arg Pro Gln Met Thr Phe Gly
1               5                   10                  15

Arg Leu Gln

<210> SEQ ID NO 33
<211> LENGTH: 22
<212> TYPE: PRT
<213> ORGANISM: Homo sapiens

<400> SEQUENCE: 33

Pro Gln Met Thr Phe Gly Arg Leu Gln Gly Ile Ser Pro Lys Ile Met
1               5                   10                  15

Pro Lys Lys Pro Ala Glu
            20

<210> SEQ ID NO 34
<211> LENGTH: 22
<212> TYPE: PRT
<213> ORGANISM: Homo sapiens

<400> SEQUENCE: 34

Pro Lys Ile Met Pro Lys Lys Pro Ala Glu Glu Gly Asn Asp Ser Glu
1               5                   10                  15

Glu Val Pro Glu Ala Ser
            20

<210> SEQ ID NO 35
<211> LENGTH: 22
<212> TYPE: PRT
<213> ORGANISM: Homo sapiens

<400> SEQUENCE: 35

Asn Asp Ser Glu Glu Val Pro Glu Ala Ser Gly Pro Gln Asn Asp Gly
1               5                   10                  15

Lys Glu Leu Cys Pro Pro
            20

<210> SEQ ID NO 36
<211> LENGTH: 22
<212> TYPE: PRT
<213> ORGANISM: Homo sapiens

<400> SEQUENCE: 36

Gln Asn Asp Gly Lys Glu Leu Cys Pro Pro Gly Lys Pro Thr Thr Ser
1               5                   10                  15

Glu Lys Ile His Glu Arg
            20
```

```
<210> SEQ ID NO 37
<211> LENGTH: 22
<212> TYPE: PRT
<213> ORGANISM: Homo sapiens

<400> SEQUENCE: 37

Pro Thr Thr Ser Glu Lys Ile His Glu Arg Ser Gly Pro Lys Arg Gly
1               5                   10                  15

Glu His Ala Trp Thr His
            20

<210> SEQ ID NO 38
<211> LENGTH: 22
<212> TYPE: PRT
<213> ORGANISM: Homo sapiens

<400> SEQUENCE: 38

Pro Lys Arg Gly Glu His Ala Trp Thr His Arg Leu Arg Glu Arg Lys
1               5                   10                  15

Gln Leu Val Ile Tyr Glu
            20

<210> SEQ ID NO 39
<211> LENGTH: 20
<212> TYPE: PRT
<213> ORGANISM: Homo sapiens

<400> SEQUENCE: 39

Arg Glu Arg Lys Gln Leu Val Ile Tyr Glu Glu Ile Ser Asp Pro Glu
1               5                   10                  15

Glu Asp Asp Glu
            20

<210> SEQ ID NO 40
<211> LENGTH: 22
<212> TYPE: PRT
<213> ORGANISM: Homo sapiens

<400> SEQUENCE: 40

Asp Asp Ala Lys Ala Ser Glu Lys Arg Ser Lys Ala Phe Asp Asp Ile
1               5                   10                  15

Ala Thr Tyr Phe Ser Lys
            20

<210> SEQ ID NO 41
<211> LENGTH: 22
<212> TYPE: PRT
<213> ORGANISM: Homo sapiens

<400> SEQUENCE: 41

Val Gly Ala Gln Ile Pro Glu Lys Ile Gln Lys Ala Phe Asp Asp Ile
1               5                   10                  15

Ala Lys Tyr Phe Ser Lys
            20

<210> SEQ ID NO 42
<211> LENGTH: 22
<212> TYPE: PRT
<213> ORGANISM: Homo sapiens
```

```
<400> SEQUENCE: 42

Asp Asp Ala Gln Ile Ser Glu Lys Leu Arg Lys Ala Phe Asp Asp Ile
1               5                   10                  15

Ala Lys Tyr Phe Ser Lys
            20

<210> SEQ ID NO 43
<211> LENGTH: 22
<212> TYPE: PRT
<213> ORGANISM: Homo sapiens

<400> SEQUENCE: 43

Val Gly Ser Gln Ile Pro Glu Lys Met Gln Lys His Pro Trp Arg Gln
1               5                   10                  15

Val Cys Asp Arg Gly Ile
            20

<210> SEQ ID NO 44
<211> LENGTH: 22
<212> TYPE: PRT
<213> ORGANISM: Homo sapiens

<400> SEQUENCE: 44

Val Gly Ser Gln Ile Pro Glu Lys Met Gln Lys Ala Phe Asp Asp Ile
1               5                   10                  15

Ala Lys Tyr Phe Ser Glu
            20

<210> SEQ ID NO 45
<211> LENGTH: 22
<212> TYPE: PRT
<213> ORGANISM: Homo sapiens

<400> SEQUENCE: 45

Asp Asp Ala Lys Ala Ser Glu Lys Arg Ser Lys Ala Phe Asp Asp Ile
1               5                   10                  15

Ala Lys Tyr Phe Ser Lys
            20

<210> SEQ ID NO 46
<211> LENGTH: 22
<212> TYPE: PRT
<213> ORGANISM: Homo sapiens

<400> SEQUENCE: 46

Ala Gly Ala Gln Ile Pro Glu Lys Ile Gln Lys Ser Phe Asp Asp Ile
1               5                   10                  15

Ala Lys Tyr Phe Ser Lys
            20

<210> SEQ ID NO 47
<211> LENGTH: 22
<212> TYPE: PRT
<213> ORGANISM: Homo sapiens

<400> SEQUENCE: 47

Asp Asp Asp Lys Ala Ser Glu Lys Arg Ser Lys Ala Phe Asn Asp Ile
1               5                   10                  15

Ala Thr Tyr Phe Ser Lys
            20
```

```
-continued

<210> SEQ ID NO 48
<211> LENGTH: 22
<212> TYPE: PRT
<213> ORGANISM: Homo sapiens

<400> SEQUENCE: 48

Ala Gly Ser Gln Ile Pro Glu Lys Ile Gln Lys Ala Phe Asp Asp Ile
1               5                   10                  15

Ala Lys Tyr Phe Ser Lys
            20
```